(12) United States Patent
Fram

(10) Patent No.: US 11,094,416 B2
(45) Date of Patent: Aug. 17, 2021

(54) INTELLIGENT MANAGEMENT OF COMPUTERIZED ADVANCED PROCESSING

(71) Applicant: INTERNATIONAL BUSINESS MACHINES CORPORATION, Armonk, NY (US)

(72) Inventor: Evan K. Fram, Paradise Valley, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/817,963

(22) Filed: Mar. 13, 2020

(65) Prior Publication Data
US 2020/0219613 A1    Jul. 9, 2020

Related U.S. Application Data

(62) Division of application No. 15/188,872, filed on Jun. 21, 2016, now Pat. No. 10,665,342, which is a
(Continued)

(51) Int. Cl.
G16H 40/63 (2018.01)
G16H 50/20 (2018.01)
(Continued)

(52) U.S. Cl.
CPC .......... *G16H 40/63* (2018.01); *G06F 3/0481* (2013.01); *G06F 3/04842* (2013.01);
(Continued)

(58) Field of Classification Search
None
See application file for complete search history.

(56) References Cited

U.S. PATENT DOCUMENTS 4,672,683 A    6/1987    Matsueda
5,123,056 A    6/1992    Wilson
(Continued)

FOREIGN PATENT DOCUMENTS

WO    WO 2007/131157    11/2007

OTHER PUBLICATIONS

US 7,801,341 B2, 09/2010, Fram et al. (withdrawn)
(Continued)

*Primary Examiner* — Anand P Bhatnagar
(74) *Attorney, Agent, or Firm* — Michael Best & Friedrich LLP

(57) ABSTRACT

Systems and methods are disclosed for automatically managing how and when computerized advanced processing techniques (for example, CAD and/or other image processing) are used. In some embodiments, the systems and methods discussed herein allow users, such as radiologists, to efficiently interact with a wide variety of computerized advanced processing ("CAP") techniques using computing devices ranging from picture archiving and communication system ("PACS") workstations to handheld devices such as smartphone and tablets. Furthermore, the systems and methods may, in various embodiments, automatically manage how data associated with these CAP techniques (for example, results of application of one or more computerized advanced processing techniques) are used, such as how data associated with the computerized analyses is reported, whether comparisons to prior abnormalities should be automatically initiated, whether the radiologist should be alerted of important findings, and the like.

3 Claims, 9 Drawing Sheets

Related U.S. Application Data division of application No. 14/139,068, filed on Dec. 23, 2013, now Pat. No. 9,495,604.

(60) Provisional application No. 61/750,662, filed on Jan. 9, 2013.

(51) Int. Cl.
*G16H 30/20* (2018.01)
*G16H 30/40* (2018.01)
*G06T 7/00* (2017.01)
*G06F 3/0481* (2013.01)
*G06F 3/0484* (2013.01)
*G06T 1/00* (2006.01)

(52) U.S. Cl.
CPC .......... *G06T 1/0007* (2013.01); *G06T 7/0012* (2013.01); *G16H 30/20* (2018.01); *G16H 30/40* (2018.01); *G16H 50/20* (2018.01); *G06T 2200/24* (2013.01)

(56) References Cited

U.S. PATENT DOCUMENTS

| | | | |
|---|---|---|---|
| 5,172,419 A | 12/1992 | Manian | |
| 5,179,651 A | 1/1993 | Taaffe et al. | |
| 5,431,161 A | 7/1995 | Ryals et al. | |
| 5,452,416 A | 9/1995 | Hilton et al. | |
| 5,515,375 A | 5/1996 | DeClerck | |
| 5,542,003 A | 7/1996 | Wofford | |
| 5,671,353 A | 9/1997 | Tian et al. | |
| 5,734,915 A | 3/1998 | Roewer | |
| 5,740,267 A | 4/1998 | Echerer et al. | |
| 5,779,634 A | 7/1998 | Ema et al. | |
| 5,807,256 A | 9/1998 | Taguchi | |
| 5,835,030 A | 11/1998 | Tsutsui et al. | |
| 5,852,646 A | 12/1998 | Klotz et al. | |
| 5,857,030 A | 1/1999 | Gaborski | |
| 5,867,322 A | 2/1999 | Morton | |
| 5,926,568 A | 7/1999 | Chaney et al. | |
| 5,954,650 A | 9/1999 | Saito et al. | |
| 5,976,088 A | 11/1999 | Urbano et al. | |
| 5,986,662 A * | 11/1999 | Argiro | G16H 15/00 345/424 |
| 5,987,345 A | 11/1999 | Engelmann et al. | |
| 5,995,644 A | 11/1999 | Lai et al. | |
| 6,008,813 A | 12/1999 | Lauer et al. | |
| 6,115,486 A | 9/2000 | Cantoni | |
| 6,128,002 A | 10/2000 | Leiper | |
| 6,130,671 A | 10/2000 | Agiro | |
| 6,151,581 A | 11/2000 | Kraftson et al. | |
| 6,175,643 B1 | 1/2001 | Lai et al. | |
| 6,177,937 B1 | 1/2001 | Stockham et al. | |
| 6,185,320 B1 | 2/2001 | Bick et al. | |
| 6,210,327 B1 | 4/2001 | Brackett et al. | |
| 6,211,795 B1 | 4/2001 | Izuta | |
| 6,211,884 B1 | 4/2001 | Knittel et al. | |
| 6,219,059 B1 | 4/2001 | Argiro | |
| 6,219,061 B1 | 4/2001 | Laurer et al. | |
| 6,243,095 B1 | 6/2001 | Shile et al. | |
| 6,243,098 B1 | 6/2001 | Laurer et al. | |
| 6,249,594 B1 | 6/2001 | Hibbard | |
| 6,262,740 B1 | 7/2001 | Laurer et al. | |
| 6,266,733 B1 | 7/2001 | Knittel et al. | |
| 6,269,379 B1 | 7/2001 | Hiyama et al. | |
| 6,297,799 B1 | 10/2001 | Knittel et al. | |
| 6,304,667 B1 | 10/2001 | Reitano | |
| 6,310,620 B1 | 10/2001 | Laurer et al. | |
| 6,313,841 B1 | 11/2001 | Ogata et al. | |
| 6,342,885 B1 | 1/2002 | Knittel et al. | |
| 6,347,329 B1 | 2/2002 | Evans | |
| 6,351,547 B1 | 2/2002 | Johnson et al. | |
| 6,356,265 B1 | 3/2002 | Knittel et al. | |
| 6,369,816 B1 | 4/2002 | Knittel et al. | |
| 6,383,135 B1 | 5/2002 | Chikovani et al. | |
| 6,388,687 B1 | 5/2002 | Brackett et al. | |
| 6,404,429 B1 | 6/2002 | Knittel | |
| 6,407,737 B1 | 6/2002 | Zhao et al. | |
| 6,411,296 B1 | 6/2002 | Knittel et al. | |
| 6,421,057 B1 | 7/2002 | Laurer et al. | |
| 6,424,346 B1 | 7/2002 | Correll et al. | |
| 6,424,996 B1 | 7/2002 | Killlcommons et al. | |
| 6,426,749 B1 | 7/2002 | Knittel et al. | |
| 6,427,022 B1 | 7/2002 | Craine et al. | |
| 6,438,533 B1 | 8/2002 | Spackman et al. | |
| 6,463,169 B1 | 10/2002 | Ino et al. | |
| 6,476,810 B1 | 11/2002 | Simha et al. | |
| 6,512,517 B1 | 1/2003 | Knittel et al. | |
| 6,532,299 B1 | 3/2003 | Sachdeva et al. | |
| 6,532,311 B1 | 3/2003 | Pritt | |
| 6,556,695 B1 | 4/2003 | Packer et al. | |
| 6,556,724 B1 | 4/2003 | Chang et al. | |
| 6,563,950 B1 | 5/2003 | Wiskott et al. | |
| 6,574,629 B1 | 6/2003 | Cooke, Jr. et al. | |
| 6,577,753 B2 | 6/2003 | Ogawa | |
| 6,603,494 B1 | 8/2003 | Banks et al. | |
| 6,604,115 B1 | 8/2003 | Gary, Jr. | |
| 6,606,171 B1 | 8/2003 | Renk et al. | |
| 6,614,447 B1 | 9/2003 | Bhatia et al. | |
| 6,618,060 B1 | 9/2003 | Brackett | |
| 6,621,918 B1 | 9/2003 | Hu et al. | |
| 6,630,937 B2 | 10/2003 | Kallergi et al. | |
| 6,650,766 B1 | 11/2003 | Rogers | |
| 6,654,012 B1 | 11/2003 | Lauer et al. | |
| 6,657,655 B1 | 12/2003 | Iizuka et al. | |
| 6,678,764 B2 | 1/2004 | Parvelescu et al. | |
| 6,680,735 B1 | 1/2004 | Seiler et al. | |
| 6,683,933 B2 | 1/2004 | Saito et al. | |
| 6,697,067 B1 | 2/2004 | Callahan et al. | |
| 6,697,506 B1 | 2/2004 | Oian et al. | |
| 6,714,623 B2 | 3/2004 | Sako et al. | |
| 6,734,880 B2 | 5/2004 | Chang et al. | |
| 6,760,755 B1 | 7/2004 | Brackett | |
| 6,775,402 B2 | 8/2004 | Bacus et al. | |
| 6,778,689 B1 | 8/2004 | Aksit et al. | |
| 6,785,410 B2 | 8/2004 | Vining et al. | |
| 6,820,093 B2 | 11/2004 | de la Huerga | |
| 6,820,100 B2 | 11/2004 | Funahashi | |
| 6,826,297 B2 | 11/2004 | Saito et al. | |
| 6,829,377 B2 | 12/2004 | Milioto | |
| 6,864,794 B2 | 3/2005 | Betz | |
| 6,886,133 B2 | 4/2005 | Bailey et al. | |
| 6,891,920 B1 | 5/2005 | Minyard et al. | |
| 6,894,707 B2 | 5/2005 | Nemoto | |
| 6,909,436 B1 | 6/2005 | Pianykh et al. | |
| 6,909,795 B2 | 6/2005 | Tecotzky et al. | |
| 6,919,975 B1 | 6/2005 | Iizuka et al. | |
| 6,917,696 B2 | 7/2005 | Soenksen | |
| 6,988,075 B1 | 1/2006 | Hacker | |
| 6,996,205 B2 | 2/2006 | Capolunghi et al. | |
| 7,016,952 B2 | 3/2006 | Mullen et al. | |
| 7,022,073 B2 | 4/2006 | Fan et al. | |
| 7,027,633 B2 | 4/2006 | Foran et al. | |
| 7,031,504 B1 | 4/2006 | Argiro et al. | |
| 7,031,846 B2 | 4/2006 | Kaushikkar et al. | |
| 7,039,723 B2 | 5/2006 | Hu et al. | |
| 7,043,474 B2 | 5/2006 | Mojsilovic et al. | |
| 7,047,235 B2 | 5/2006 | Yang et al. | |
| 7,050,620 B2 | 5/2006 | Heckman | |
| 7,054,473 B1 | 5/2006 | Roehrig et al. | |
| 7,058,901 B1 | 6/2006 | Hafey et al. | |
| 7,092,572 B2 | 8/2006 | Huang et al. | |
| 7,103,205 B2 | 9/2006 | Wang et al. | |
| 7,106,479 B2 | 9/2006 | Roy et al. | |
| 7,110,616 B2 | 9/2006 | Ditt et al. | |
| 7,113,186 B2 | 9/2006 | Kim et al. | |
| 7,123,684 B2 | 10/2006 | Jing et al. | |
| 7,136,064 B2 | 11/2006 | Zuiderveld | |
| 7,139,416 B2 | 11/2006 | Vuylsteke | |
| 7,149,334 B2 | 12/2006 | Dehmeshki | |
| 7,155,043 B2 | 12/2006 | Daw | |
| 7,162,623 B2 * | 1/2007 | Yngvesson | G06T 1/00 345/619 |
| 7,170,532 B2 | 1/2007 | Sako | |

(56) References Cited

U.S. PATENT DOCUMENTS

| | | |
|---|---|---|
| 7,174,054 B2 | 2/2007 | Manber et al. |
| 7,209,149 B2 | 4/2007 | Jogo |
| 7,209,578 B2 | 4/2007 | Saito et al. |
| 7,212,661 B2 | 5/2007 | Samara et al. |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummel, Jr. et al. |
| 7,272,610 B2 | 9/2007 | Tones |
| 7,277,564 B2 | 10/2007 | Yarger et al. |
| 7,346,199 B2 | 3/2008 | Pfaff |
| 7,362,324 B2 | 4/2008 | Iizuka et al. |
| 7,366,992 B2 | 4/2008 | Thomas, III |
| 7,379,578 B2 | 5/2008 | Soussaline et al. |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |
| 7,516,417 B2 | 4/2009 | Amador et al. |
| 7,519,591 B2 | 4/2009 | Landi et al. |
| 7,523,505 B2 | 4/2009 | Menschik et al. |
| 7,525,554 B2 | 4/2009 | Morita et al. |
| 7,526,114 B2 | 4/2009 | Xia et al. |
| 7,526,132 B2 | 4/2009 | Koenig |
| 7,545,965 B2 | 6/2009 | Suzuki et al. |
| 7,574,029 B2 | 8/2009 | Peterson et al. |
| 7,583,861 B2 | 9/2009 | Hanna et al. |
| 7,590,272 B2 | 9/2009 | Brejl et al. |
| 7,599,534 B2 * | 10/2009 | Krishnan ............ G06T 7/0012 382/128 |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,413 B2 | 2/2010 | Partovi et al. |
| 7,660,448 B2 | 2/2010 | Collins et al. |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,885,828 B2 * | 2/2011 | Glaser-Seidnitzer ...................... G16H 30/40 705/3 |
| 7,899,514 B1 | 3/2011 | Kirkland |
| 7,920,152 B2 | 4/2011 | Fram et al. |
| 7,941,462 B2 * | 5/2011 | Akinyemi ................ G06T 7/12 707/803 |
| 7,983,614 B2 | 5/2011 | Reicher |
| 7,965,408 B2 | 6/2011 | Samari |
| 7,965,907 B2 | 6/2011 | Takekoshi |
| 7,970,188 B2 | 6/2011 | Mahesh et al. |
| 7,970,625 B2 | 6/2011 | Reicher et al. |
| 7,991,210 B2 | 8/2011 | Peterson et al. |
| 7,992,100 B2 | 8/2011 | Lundstrom et al. |
| 7,995,821 B2 | 8/2011 | Nakamura |
| 8,019,138 B2 | 9/2011 | Reicher et al. |
| 8,045,214 B2 | 10/2011 | Samari |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |
| 8,217,966 B2 | 7/2012 | Fram et al. |
| 8,244,014 B2 | 8/2012 | Reicher et al. |
| 8,249,687 B2 | 8/2012 | Peterson et al. |
| 8,262,572 B2 | 9/2012 | Chono |
| 8,292,811 B2 | 10/2012 | Relkuntwar et al. |
| 8,297,147 B2 * | 10/2012 | Wu ........................ A47C 7/00 74/502.2 |
| 8,298,147 B2 | 10/2012 | Huennekens et al. |
| 8,370,293 B2 | 2/2013 | Iwase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,452,063 B2 | 5/2013 | Wojton et al. |
| 8,457,990 B1 | 6/2013 | Reicher et al. |
| 8,520,978 B2 | 8/2013 | Jakobovits |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,771,189 B2 | 7/2014 | Ionasec et al. |
| 8,797,350 B2 | 8/2014 | Fram |
| 8,879,807 B2 | 11/2014 | Fram et al. |
| 8,913,808 B2 | 12/2014 | Reicher et al. |
| 8,954,884 B1 | 2/2015 | Barger |
| 8,976,190 B1 | 3/2015 | Westerhoff et al. |
| 9,042,617 B1 | 5/2015 | Reicher et al. |
| 9,075,899 B1 | 7/2015 | Reicher |
| 9,092,551 B1 | 7/2015 | Reicher |
| 9,092,727 B1 | 7/2015 | Reicher |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B1 | 11/2016 | Fram et al. |
| 9,536,324 B1 | 1/2017 | Fram |
| 9,542,082 B1 | 1/2017 | Reicher et al. |
| 9,672,477 B1 | 6/2017 | Reicher et al. |
| 9,684,762 B2 | 6/2017 | Reicher et al. |
| 9,727,938 B1 | 8/2017 | Reicher et al. |
| 9,734,576 B2 | 8/2017 | Fram et al. |
| 9,754,074 B1 | 9/2017 | Reicher et al. |
| 9,836,202 B1 | 12/2017 | Reicher et al. |
| 9,892,341 B2 | 2/2018 | Reicher et al. |
| 9,934,568 B2 | 4/2018 | Reicher et al. |
| 1,009,611 A1 | 10/2018 | Fram et al. |
| 1,015,768 A1 | 12/2018 | Reicher et al. |
| 1,038,761 A1 | 8/2019 | Wu et al. |
| 1,054,076 A1 | 8/2019 | Wu et al. |
| 1,043,744 A1 | 10/2019 | Reicher et al. |
| 1,043,835 A1 | 10/2019 | Fram et al. |
| 1,057,990 A1 | 3/2020 | Reicher |
| 1,059,268 A1 | 3/2020 | Reicher et al. |
| 1,060,734 A1 | 3/2020 | Reicher et al. |
| 1,061,461 A1 | 4/2020 | Fram et al. |
| 1,066,534 A1 | 5/2020 | Fram |
| 1,067,251 A1 | 6/2020 | Fram |
| 2001/0016822 A1 | 8/2001 | Bessette |
| 2001/0041991 A1 | 11/2001 | Segal et al. |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0054038 A1 | 5/2002 | Nemoto |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0099273 A1 | 7/2002 | Bocionek et al. |
| 2002/0103673 A1 | 8/2002 | Atwood |
| 2002/0103827 A1 | 8/2002 | Sesek |
| 2002/0106119 A1 | 8/2002 | Foran et al. |
| 2002/0106373 A1 | 8/2002 | Hillman et al. |

(56) References Cited

U.S. PATENT DOCUMENTS

| | | |
|---|---|---|
| 2002/0110285 A1 | 8/2002 | Wang et al. |
| 2002/0144697 A1 | 10/2002 | Betz |
| 2002/0145941 A1 | 10/2002 | Poland et al. |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0188637 A1 | 12/2002 | Bailey et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0053668 A1 | 3/2003 | Ditt et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140044 A1 | 7/2003 | Mok et al. |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0195416 A1 | 10/2003 | Toth |
| 2003/0204420 A1 | 10/2003 | Wilkes et al. |
| 2003/0215120 A1* | 11/2003 | Uppaluri ............... A61B 6/505 382/128 |
| 2003/0215122 A1 | 11/2003 | Tanaka |
| 2004/0008900 A1 | 1/2004 | Jabri et al. |
| 2004/0015703 A1 | 1/2004 | Madison et al. |
| 2004/0024303 A1 | 2/2004 | Banks et al. |
| 2004/0027359 A1 | 2/2004 | Aharon et al. |
| 2004/0061889 A1* | 4/2004 | Wood ............... A61B 5/415 358/1.15 |
| 2004/0068170 A1 | 4/2004 | Wang et al. |
| 2004/0077952 A1 | 4/2004 | Rafter et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0122787 A1* | 6/2004 | Avinash ............... G16H 50/20 706/50 |
| 2004/0141661 A1 | 7/2004 | Hanna et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0197015 A1 | 10/2004 | Fan et al. |
| 2004/0202387 A1 | 10/2004 | Yngvesson |
| 2004/0243435 A1 | 12/2004 | Williams |
| 2004/0252871 A1 | 12/2004 | Tecotzlcky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamoorthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0203775 A1 | 9/2005 | Chesbrough |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0259118 A1 | 11/2005 | Mojaver et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0093027 A1 | 5/2006 | Draving et al. |
| 2006/0093139 A1 | 5/2006 | Quan |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111937 A1 | 5/2006 | Yarger et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey et al. |
| 2006/0188134 A1 | 8/2006 | Quist |
| 2006/0230072 A1 | 10/2006 | Partovi et al. |
| 2006/0238546 A1 | 10/2006 | Handley et al. |
| 2006/0239573 A1 | 10/2006 | Novatzky et al. |
| 2006/0241979 A1 | 10/2006 | Sato et al. |
| 2006/0267976 A1 | 11/2006 | Saito et al. |
| 2006/0274145 A1 | 12/2006 | Reiner |
| 2006/0276708 A1 | 12/2006 | Peterson et al. |
| 2006/0277075 A1 | 12/2006 | Salwan |
| 2006/0282408 A1 | 12/2006 | Wisely et al. |
| 2006/0282447 A1 | 12/2006 | Hollebeek |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson et al. |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper et al. |
| 2007/0237380 A1 | 10/2007 | Iwase et al. |
| 2007/0239481 A1 | 10/2007 | DiSilvestro et al. |
| 2007/0245308 A1 | 10/2007 | Hill et al. |
| 2007/0270695 A1 | 11/2007 | Keen |
| 2008/0016111 A1 | 1/2008 | Keen |
| 2008/0019581 A1 | 1/2008 | Gkanatsios et al. |
| 2008/0021877 A1 | 1/2008 | Saito et al. |

(56) References Cited

U.S. PATENT DOCUMENTS

| | | |
|---|---|---|
| 2008/0031507 A1* | 2/2008 | Uppaluri ............... G16H 30/20 382/132 |
| 2008/0059245 A1 | 3/2008 | Sakaida et al. |
| 2008/0097186 A1* | 4/2008 | Biglieri ................ G16H 30/20 600/407 |
| 2008/0100612 A1 | 5/2008 | Dastmalchi et al. |
| 2008/0103828 A1 | 5/2008 | Squilla et al. |
| 2008/0118120 A1 | 5/2008 | Wegenkittl et al. |
| 2008/0125846 A1 | 5/2008 | Battle et al. |
| 2008/0126982 A1 | 5/2008 | Sadikali et al. |
| 2008/0130966 A1 | 6/2008 | Crucs |
| 2008/0133526 A1 | 6/2008 | Haitani et al. |
| 2008/0136838 A1 | 6/2008 | Goede et al. |
| 2008/0136868 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0022386 A1 | 1/2009 | Karau et al. |
| 2009/0028410 A1 | 1/2009 | Shimazaki |
| 2009/0080719 A1 | 3/2009 | Watt |
| 2009/0091566 A1 | 4/2009 | Turney et al. |
| 2009/0094513 A1 | 4/2009 | Bay |
| 2009/0123052 A1 | 5/2009 | Ruth et al. |
| 2009/0129643 A1 | 5/2009 | Natanzon et al. |
| 2009/0129651 A1 | 5/2009 | Zagzebski et al. |
| 2009/0132586 A1 | 5/2009 | Napora et al. |
| 2009/0150481 A1 | 6/2009 | Garcia et al. |
| 2009/0164247 A1* | 6/2009 | Dobler ................. G16H 30/20 705/3 |
| 2009/0177637 A1 | 7/2009 | Hollebeek |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0297013 A1 | 12/2009 | Chaudhari |
| 2009/0326373 A1 | 12/2009 | Boese et al. |
| 2010/0053353 A1 | 3/2010 | Hunter et al. |
| 2010/0086182 A1 | 4/2010 | Luo et al. |
| 2010/0119027 A1 | 5/2010 | Peterson et al. |
| 2010/0131887 A1 | 5/2010 | Salazar-Ferrer et al. |
| 2010/0138239 A1 | 6/2010 | Reicher et al. |
| 2010/0138240 A1 | 6/2010 | Leib et al. |
| 2010/0198608 A1 | 8/2010 | Kaboff et al. |
| 2010/0201714 A1 | 8/2010 | Reicher et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram et al. |
| 2011/0019886 A1 | 1/2011 | Mizuno |
| 2011/0110572 A1 | 5/2011 | Guehring et al. |
| 2011/0267339 A1 | 11/2011 | Fram et al. |
| 2011/0293162 A1 | 12/2011 | Pajeau |
| 2011/0316873 A1 | 12/2011 | Reicher et al. |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0183191 A1* | 7/2012 | Nakamura ............ A61B 5/416 382/128 |
| 2012/0194540 A1 | 8/2012 | Reicher et al. |
| 2012/0196258 A1 | 8/2012 | Geijsen et al. |
| 2012/0208592 A1 | 8/2012 | Davis et al. |
| 2012/0284657 A1 | 11/2012 | Hafey et al. |
| 2012/0320093 A1 | 12/2012 | Zhu et al. |
| 2012/0324400 A1 | 12/2012 | Caliendo, Jr. et al. |
| 2013/0070998 A1 | 3/2013 | Shibata |
| 2013/0076681 A1 | 3/2013 | Sirpal et al. |
| 2013/0083023 A1 | 4/2013 | Fram et al. |
| 2013/0129198 A1 | 5/2013 | Sherman et al. |
| 2013/0129231 A1 | 5/2013 | Dale et al. |
| 2013/0159019 A1 | 6/2013 | Reicher et al. |
| 2013/0169661 A1 | 7/2013 | Reicher et al. |
| 2013/0195329 A1 | 8/2013 | Canda et al. |
| 2013/0198682 A1 | 8/2013 | Matas et al. |
| 2013/0297331 A1 | 11/2013 | Zuehlsdorff et al. |
| 2014/0022194 A1 | 1/2014 | Ito |
| 2014/0096049 A1 | 4/2014 | Vonshak et al. |
| 2014/0119514 A1 | 5/2014 | Miyazawa |
| 2014/0142983 A1 | 5/2014 | Backhaus et al. |
| 2014/0378810 A1 | 12/2014 | Davis et al. |
| 2015/0046349 A1 | 2/2015 | Michael, Jr. et al. |
| 2015/0101066 A1 | 4/2015 | Fram |
| 2015/0160848 A1 | 6/2015 | Gkanatsios et al. |
| 2015/0363104 A1 | 12/2015 | Ichioka et al. |
| 2016/0034110 A1 | 2/2016 | Edwards |
| 2016/0162745 A1 | 9/2016 | Cohen-Solal et al. |
| 2016/0270746 A1* | 9/2016 | Foos ...................... A61B 6/463 |
| 2016/0335395 A1 | 11/2016 | Wu et al. |
| 2017/0038951 A1 | 2/2017 | Reicher et al. |
| 2017/0039321 A1 | 2/2017 | Reicher et al. |
| 2017/0039322 A1 | 2/2017 | Reicher et al. |
| 2017/0039350 A1 | 2/2017 | Reicher et al. |
| 2017/0039705 A1 | 2/2017 | Fram et al. |
| 2017/0046014 A1 | 2/2017 | Fram |
| 2017/0046483 A1 | 2/2017 | Reicher et al. |
| 2017/0046485 A1 | 2/2017 | Reicher et al. |
| 2017/0046495 A1 | 2/2017 | Fram |
| 2017/0046870 A1 | 2/2017 | Fram et al. |
| 2017/0053404 A1 | 2/2017 | Reicher et al. |
| 2017/0200064 A1 | 7/2017 | Reicher et al. |
| 2017/0200269 A1 | 7/2017 | Reicher et al. |
| 2017/0200270 A1 | 7/2017 | Reicher et al. |
| 2017/0206324 A1 | 7/2017 | Reicher et al. |
| 2017/0239720 A1 | 8/2017 | Levin et al. |
| 2017/0293720 A1 | 10/2017 | Reicher et al. |
| 2017/0301090 A1 | 10/2017 | Fram et al. |
| 2017/0308647 A1 | 10/2017 | Reicher et al. |
| 2018/0059918 A1 | 3/2018 | Reicher et al. |
| 2018/0225824 A1 | 8/2018 | Fram et al. |
| 2019/0009371 A1 | 1/2019 | Veerasamy et al. |

OTHER PUBLICATIONS

US 8,208,705 B2, 06/2012, Reicher et al. (withdrawn)
Non-Final Office Action from the U.S. Patent and Trademark Office for U.S. Appl. No. 11/179,384 dated Aug. 28, 2007 (15 pages).
Final Office Action from the U.S. Patent and Trademark Office for U.S. Appl. No. 11/179,384 dated Jun. 26, 2008 (31 pages).
Examiner Interview Summary from the U.S. Patent and Trademark Office for U.S. Appl. No. 11/179,384 dated Sep. 24, 2008 (4 pages).
Non-Final Office Action from the U.S. Patent and Trademark Office for U.S. Appl. No. 11/179,384 dated Dec. 29, 2008 (45 pages).
Examiner Interview Summary from the U.S. Patent and Trademark Office for U.S. Appl. No. 11/179,384 dated Feb. 18, 2009 (2 pages).
Final Office Action from the U.S. Patent and Trademark Office for U.S. Appl. No. 11/179,384 dated Jul. 24, 2009 (23 pages).
Advisory Action from the U.S. Patent and Trademark Office for U.S. Appl. No. 11/179,384 dated Sep. 17, 2009 (3 pages).
Notice of Allowance from the U.S. Patent and Trademark Office for U.S. Appl. No. 11/179,384 dated Nov. 3, 2009 (8 pages).
Non-Final Office Action from the U.S. Patent and Trademark Office for U.S. Appl. No. 11/265,978 dated Jul. 27, 2009 (7 pages).
Notice of Allowance from the U.S. Patent and Trademark Office for U.S. Appl. No. 11/265,978 dated Nov. 19, 2009 (6 pages).
Notice of Allowance from the U.S. Patent and Trademark Office for U.S. Appl. No. 11/265,978 dated Apr. 19, 2010 (7 pages).
Notice of Allowance from the U.S. Patent and Trademark Office for U.S. Appl. No. 11/265,978 dated May 3, 2010 (2 pages).
Notice of Allowance from the U.S. Patent and Trademark Office for U.S. Appl. No. 11/265,978 dated Aug. 3, 2010 (2 pages).
Non-Final Office Action from the U.S. Patent and Trademark Office for U.S. Appl. No. 11/265,979 dated May 13, 2009 (16 pages).
Final Office Action from the U.S. Patent and Trademark Office for U.S. Appl. No. 11/265,979 dated Dec. 22, 2009 (17 pages).
Interview Summary from the U.S. Patent and Trademark Office for U.S. Appl. No. 11/265,979 dated March 4, 2010 (3 pages).

(56) References Cited

OTHER PUBLICATIONS

Non-Final Office Action from the U.S. Patent and Trademark Office for U.S. Appl. No. 11/265,979 dated Jul. 8, 2010 (18 pages).
Interview Summary from the U.S. Patent and Trademark Office for U.S. Appl. No. 11/265,979 dated Nov. 16, 2010 (3 pages).
Final Office Action from the U.S. Patent and Trademark Office for U.S. Appl. No. 11/265,979 dated Dec. 23, 2010 (24 pages).
Notice of Allowance from the U.S. Patent and Trademark Office for U.S. Appl. No. 11/265,979 dated May 13, 2011 (14 pages).
Interview Summary from the U.S. Patent and Trademark Office for U.S. Appl. No. 11/265,979 dated Mar. 17, 2011 (3 pages).
Supplemental Notice of Allowabilliaty from the U.S. Patent and Trademark Office for U.S. Appl. No. 11/265,979 dated May 26, 2011 (4 pages).
Non-Final Office Action from the U.S. Patent and Trademark Office for U.S. Appl. No. 11/268,261 dated Oct. 1, 2009 (35 pages).
Interview Summary from the U.S. Patent and Trademark Office for U.S. Appl. No. 11/268,261 dated Jan. 25, 2010 (3 pages).
Notice of Allowance from the U.S. Patent and Trademark Office for U.S. Appl. No. 11/268,261 dated Feb. 2, 2010 (12 pages).
Interview Summary from the U.S. Patent and Trademark Office for U.S. Appl. No. 11/268,261 dated. May 14, 2010 (2 pages).
Notice of Allowance from the U.S. Patent and Trademark Office for U.S. Appl. No. 11/268,261 dated May 17, 2010 (8 pages).
Supplemental Notice of Allowabilliaty from the U.S. Patent and Trademark Office for U.S. Appl. No. 11/268,261 dated Aug. 6, 2010 (4 pages).
Notice of Allowance from the U.S. Patent and Trademark Office for U.S. Appl. No. 11/268,261 dated Oct. 8, 2010 (6 pages).
Issue Notice from the U.S. Patent and Trademark Office for U.S. Appl. No. 11/268,261 dated Sep. 1, 2010 (1 page).
Notice of Allowance from the U.S. Patent and Trademark Office for U.S. Appl. No. 11/268,261 dated Dec. 3, 2010 (6 pages).
Supplemental Notice of Allowabilliaty from the U.S. Patent and Trademark Office for U.S. Appl. No. 11/268,261 dated Jan. 6, 2011 (3 pages).
Non-Final Office Action from the U.S. Patent and Trademark Office for U.S. Appl. No. 11/268,262 dated Aug. 24, 2009 (17 pages).
Interview Summary from the U.S. Patent and Trademark Office for U.S. Appl. No. 11/268,262 dated Nov. 24, 2009 (4 pages).
Non-Final Office Action from the U.S. Patent and Trademark Office for U.S. Appl. No. 11/268,262 dated Apr. 16, 2010 (22 pages).
Interview Summary from the U.S. Patent and Trademark Office for U.S. Appl. No. 11/268,262 dated. May 12, 2010 (4 pages).
Final Office Action from the U.S. Patent and Trademark Office for U.S. Appl. No. 11/268,262 dated Oct. 28, 2010 (12 pages).
Notice of Allowance from the U.S. Patent and Trademark Office for U.S. Appl. No. 11/268,262 dated Dec. 1, 2010 (8 pages).
Interview Summary from the U.S. Patent and Trademark Office for U.S. Appl. No. 11/268,262 dated Dec. 1, 2010 (4 pages).
Notice of Allowance from the U.S. Patent and Trademark Office for U.S. Appl. No. 11/268,262 dated Feb. 25, 2011 (5 pages).
Non-Final Office Action from the U.S. Patent and Trademark Office for U.S. Appl. No. 11/942,674 dated May 26, 2010 (13 pages).
Interview Summary from the U.S. Patent and Trademark Office for U.S. Appl. No. 11/942,674 dated. Jul. 26, 2010 (3 pages).
Final Office Action from the U.S. Patent and Trademark Office for U.S. Appl. No. 11/942,674 dated Nov. 26, 2010 (19 pages).
Interview Summary from the U.S. Patent and Trademark Office for U.S. Appl. No. 11/942,674 dated Mar. 2, 2011 (3 pages).
Notice of Allowance from the U.S. Patent and Trademark Office for U.S. Appl. No. 11/942,674 dated Apr. 1, 2011 (9 pages).
Non-Final Office Action from the U.S. Patent and Trademark Office for U.S. Appl. No. 11/942,687 dated Sep. 16, 2010.
Interview Summary from the U.S. Patent and Trademark Office for U.S. Appl. No. 11/942,687 dated Dec. 3, 2010.
Final Office Action from the U.S. Patent and Trademark Office for U.S. Appl. No. 11/942,687 dated Apr. 5, 2011.
Interview Summary from the U.S. Patent and Trademark Office for U.S. Appl. No. 11/942,687 dated Jun. 10, 2011 (3 pages).
Office Action from the U.S. Patent and Trademark Office for U.S. Appl. No. 11/942,687 dated Mar. 13, 2014.
Applicant-Initiated Interview Summary from the U.S. Patent and Trademark Office for U.S. Appl. No. 11/942,687 dated Jun. 17, 2014 (3 pages).
Office Action from the U.S. Patent and Trademark Office for U.S. Appl. No. 11/942,687 dated Jul. 18, 2014.
Final Office Action from the U.S. Patent and Trademark Office for U.S. Appl. No. 11/942,687 dated Jan. 5, 2015.
Applicant-Initiated Interview Summary from the U.S. Patent and Trademark Office for U.S. Appl. No. 11/942,687 dated Mar. 4, 2015 (3 pages).
Examiner's Answer to Appeal Brief from the U.S. Patent and Trademark Office for U.S. Appl. No. 11/942,687 dated Feb. 25, 2016 (11 pages).
Patent Board Decision from the U.S. Patent and Trademark Office for U.S. Appl. No. 11/942,687 dated Dec. 22, 2017 (13 pages).
Non-Final Office Action from the U.S. Patent and Trademark Office for U.S. Appl. No. 11/944,000 dated Sep. 29, 2010.
Examiner Interview Summary from the U.S. Patent and Trademark Office for U.S. Appl. No. 11/944,000 dated Feb. 4, 2011 (3 pages).
Final Office Action from the U.S. Patent and Trademark Office for U.S. Appl. No. 11/944,000 dated Apr. 20, 2011.
Interview Summary from the U.S. Patent and Trademark Office for U.S. Appl. No. 11/944,000 dated Jun. 7, 2011.
Advisory Action from the U.S. Patent and Trademark Office for U.S. Appl. No. 11/944,000 dated Aug. 1, 2011 (3 pages).
Non-Final Office Action from the U.S. Patent and Trademark Office for U.S. Appl. No. 11/944,000 dated Oct. 5, 2012 (11 pages).
Appeal Brief from the U.S. Patent and Trademark Office for U.S. Appl. No. 11/944,000 dated Mar. 4, 2013.
Examiner's Answer to Appeal Brief from the U.S. Patent and Trademark Office for U.S. Appl. No. 11/944,000 dated Jun. 26, 2013 (14 pages).
Patent Board Decision from the U.S. Patent and Trademark Office for U.S. Appl. No. 11/944,000 dated Mar. 23, 2016 (8 pages).
Office Action from the U.S. Patent and Trademark Office for U.S. Appl. No. 11/944,000 dated Jul. 15, 2016.
Notice of Allowance from the U.S. Patent and Trademark Office for U.S. Appl. No. 11/944,000 dated Jan. 30, 2017 (12 pages).
Non-Final Office Action from the U.S. Patent and Trademark Office for U.S. Appl. No. 11/944,027 dated Apr. 14, 2010.
Interview Summary from the U.S. Patent and Trademark Office for U.S. Appl. No. 11/944,027 dated May 13, 2010.
Final Office Action from the U.S. Patent and Trademark Office for U.S. Appl. No. 11/944,027 dated Dec. 23, 2010.
Interview Summary from the U.S. Patent and Trademark Office for U.S. Appl. No. 11/944,027 dated Mar. 31, 2011.
Office Action from the U.S. Patent and Trademark Office for U.S. Appl. No. 11/944,027 dated Apr. 19, 2012.
Interview Summary from the U.S. Patent and Trademark Office for U.S. Appl. No. 11/944,027 dated Jun. 28, 2012.
Final Office Action from the U.S. Patent and Trademark Office for U.S. Appl. No. 11/944,027 dated Oct. 22, 2012.
Notice of Allowance from the U.S. Patent and Trademark Office for U.S. Appl. No. 11/944,027 dated Jun. 5, 2013.
Office Action from the U.S. Patent and Trademark Office for U.S. Appl. No. 12/622,404 dated Feb. 3, 2012.
Interview Summary from the U.S. Patent and Trademark Office for U.S. Appl. No. 12/622,404 dated May 8, 2012.
Final Office Action from the U.S. Patent and Trademark Office for U.S. Appl. No. 12/622,404 dated Aug. 6, 2012.
Notice of Allowance from the U.S. Patent and Trademark Office for U.S. Appl. No. 12/622,404 dated Oct. 15, 2012.
Non-Final Office Action from the U.S. Patent and Trademark Office for U.S. Appl. No. 12/702,976 dated Aug. 18, 2010 (17 pages).
Interview Summary from the U.S. Patent and Trademark Office for U.S. Appl. No. 12/702,976 dated Dec. 1, 2010 (4 pages).
Final Office Action from the U.S. Patent and Trademark Office for U.S. Appl. No. 12/702,976 dated Feb. 17, 2011 (13 pages).
Interview Summary from the U.S. Patent and Trademark Office for U.S. Appl. No. 12/702,976 dated May 31, 2011 (3 pages).

(56) References Cited

OTHER PUBLICATIONS

Notice of Allowance from the U.S. Patent and Trademark Office for U.S. Appl. No. 12/702,976 dated Jul. 20, 2011 (7 pages).
Non-Final Office Action from the U.S. Patent and Trademark Office for U.S. Appl. No. 12/857,915 dated May 16, 2011 (26 pages).
Applicant-Initiated Interview Summary from the U.S. Patent and Trademark Office for U.S. Appl. No. 12/857,915 dated Sep. 6, 2011 (3 pages).
Final Office Action from the U.S. Patent and Trademark Office for U.S. Appl. No. 12/857,915 dated Dec. 15, 2011 (37 pages).
Non-Final Office Action from the U.S. Patent and Trademark Office for U.S. Appl. No. 12/857,915 dated Jun. 12, 2012 (33 pages).
Non-Final Office Action from the U.S. Patent and Trademark Office for U.S. Appl. No. 12/857,915 dated Aug. 23, 2013 (33 pages).
Applicant-Initiated Interview Summary from the U.S. Patent and Trademark Office for U.S. Appl. No. 12/857,915 dated Feb. 4, 2014 (3 pages).
Examiner-Initiated Interview Summary from the U.S. Patent and Trademark Office for U.S. Appl. No. 12/857,915 dated Jul. 3, 2014 (1 page).
Notice of Allowance from the U.S. Patent and Trademark Office for U.S. Appl. No. 12/857,915 dated Jul. 3, 2014 (19 pages).
Notice of Allowance from the U.S. Patent and Trademark Office for U.S. Appl. No. 12/857,915 dated Aug. 15, 2014 (4 pages).
Non-Final Office Action from the U.S. Patent and Trademark Office for U.S. Appl. No. 12/870,645 dated May 5, 2011 (5 pages).
Examiner Interview Summary from the U.S. Patent and Trademark Office for U.S. Appl. No. 12/870,645 dated Jun. 10, 2011 (2 pages).
Notice of Allowance from the U.S. Patent and Trademark Office for U.S. Appl. No. 12/870,645 dated Sep. 13, 2011 (8 pages).
Notice of Allowance from the U.S. Patent and Trademark Office for U.S. Appl. No. 12/870,645 dated Dec. 7, 2011 (4 pages).
Office Action from the U.S. Patent and Trademark Office for U.S. Appl. No. 12/891,543 dated Mar. 4, 2013.
Interview Summary from the U.S. Patent and Trademark Office for U.S. Appl. No. 12/891,543 dated Apr. 5, 2013.
Examiner-Initiated Interview Summary from the U.S. Patent and Trademark Office for U.S. Appl. No. 12/891,543 dated Nov. 14, 2013 (1 page).
Notice of Allowance from the U.S. Patent and Trademark Office for U.S. Appl. No. 12/891,543 dated Nov. 14, 2013 (14 pages).
Non-Final Office Action from the U.S. Patent and Trademark Office for U.S. Appl. No. 13/079,597 dated Jan. 11, 2012 (8 pages).
Notice of Allowance from the U.S. Patent and Trademark Office for U.S. Appl. No. 13/079,597 dated Apr. 25, 2012 (5 pages).
Non-Final Office Action from the U.S. Patent and Trademark Office for U.S. Appl. No. 13/118,085 dated Nov. 10, 2011 (12 pages).
Interview Summary from the U.S. Patent and Trademark Office for U.S. Appl. No. 13/118,085 dated Feb. 17, 2012 (3 pages).
Final Office Action from the U.S. Patent and Trademark Office for U.S. Appl. No. 13/118,085 dated Apr. 13, 2012 (15 pages).
Notice of Allowance from the U.S. Patent and Trademark Office for U.S. Appl. No. 13/118,085 dated Feb. 6, 2013 (11 pages).
Non-Final Office Action from the U.S. Patent and Trademark Office for U.S. Appl. No. 13/171,081 dated Jun. 8, 2012 (21 pages).
Applicant-Initiated Interview Summary from the U.S. Patent and Trademark Office for U.S. Appl. No. 13/171,081 dated Jul. 31, 2012 (3 page).
Final Office Action from the U.S. Patent and Trademark Office for U.S. Appl. No. 13/171,081 dated Oct. 12, 2012 (21 pages).
Applicant-Initiated Interview Summary from the U.S. Patent and Trademark Office for U.S. Appl. No. 13/171,081 dated Nov. 6, 2012 (3 page).
Examiner-Initiated Interview Summary from the U.S. Patent and Trademark Office for U.S. Appl. No. 13/171,081 dated Sep. 4, 2013 (1 page).
Notice of Allowance from the U.S. Patent and Trademark Office for U.S. Appl. No. 13/171,081 dated Sep. 4, 2013 (11 pages).
Non-Final Office Action from the U.S. Patent and Trademark Office for U.S. Appl. No. 13/228,349 dated Dec. 1, 2011 (17 pages).
Notice of Allowance from the U.S. Patent and Trademark Office for U.S. Appl. No. 13/228,349 dated Feb. 6, 2012 (5 pages).
Notice of Allowabilliaty from the U.S. Patent and Trademark Office for U.S. Appl. No. 13/228,349 dated Jul. 20, 2012 (3 pages).
Non-Final Office Action from the U.S. Patent and Trademark Office for U.S. Appl. No. 13/345,606 dated May 31, 2013 (12 pages).
Interview Summary from the U.S. Patent and Trademark Office for U.S. Appl. No. 13/345,606 dated Aug. 15, 2013 (3 pages).
Applicant Summary of Interview of Examiner from the U.S. Patent and Trademark Office for U.S. Appl. No. 13/345,606 dated Oct. 21, 2013 (8 pages).
Summary of Interview from the U.S. Patent and Trademark Office for U.S. Appl. No. 13/345,606 dated Oct. 21, 2013 (1 page).
Notice of Allowance from the U.S. Patent and Trademark Office for U.S. Appl. No. 13/345,606 dated Jan. 9, 2014 (7 pages).
Non-Final Office Action from the U.S. Patent and Trademark Office for U.S. Appl. No. 13/477,853 dated Dec. 11, 2013 (20 pages).
Applicant-Initiated Interview Summary from the U.S. Patent and Trademark Office for U.S. Appl. No. 13/477,853 dated Mar. 14, 2014 (3 pages).
Final Office Action from the U.S. Patent and Trademark Office for U.S. Appl. No. 13/477,853 dated Jun. 13, 2014 (13 pages).
Notice of Allowance from the U.S. Patent and Trademark Office for U.S. Appl. No. 13/477,853 dated Aug. 15, 2014 (7 pages).
Non-Final Office Action from the U.S. Patent and Trademark Office for U.S. Appl. No. 13/535,758 dated Apr. 4, 2013 (8 pages).
Notice of Allowance from the U.S. Patent and Trademark Office for U.S. Appl. No. 13/535,758 dated Aug. 23, 2013 (10 pages).
Office Action from the U.S. Patent and Trademark Office for U.S. Appl. No. 13/572,397 dated Jun. 27, 2014.
Final Office Action from the U.S. Patent and Trademark Office for U.S. Appl. No. 13/572,397 dated Jan. 13, 2015.
Notice of Allowance from the U.S. Patent and Trademark Office for U.S. Appl. No. 13/572,397 dated Mar. 19, 2015.
Notice of Allowance from the U.S. Patent and Trademark Office for U.S. Appl. No. 13/572,397 dated Jun. 29, 2015 (2 pages).
Office Action from the U.S. Patent and Trademark Office for U.S. Appl. No. 13/572,547 dated Aug. 6, 2014.
Notice of Allowance from the U.S. Patent and Trademark Office for U.S. Appl. No. 13/572,547 dated Mar. 3, 2015.
Notice of Allowance from the U.S. Patent and Trademark Office for U.S. Appl. No. 13/572,547 dated Apr. 10, 2015.
Notice of Allowance from the U.S. Patent and Trademark Office for U.S. Appl. No. 13/572,547 dated May 21, 2015.
Office Action from the U.S. Patent and Trademark Office for U.S. Appl. No. 13/572,552 dated Jul. 30, 2014.
Applicant-Initiated Interview Summary from the U.S. Patent and Trademark Office for U.S. Appl. No. 13/572,552 dated Sep. 3, 2014 (3 pages).
Final Office Action from the U.S. Patent and Trademark Office for U.S. Appl. No. 13/572,552 dated Jan. 28, 2015.
Interview Summary from the U.S. Patent and Trademark Office for U.S. Appl. No. 13/572,552 dated Apr. 23, 2015.
Notice of Allowance from the U.S. Patent and Trademark Office for U.S. Appl. No. 13/572,552 dated May 8, 2015.
Office Action from the U.S. Patent and Trademark Office for U.S. Appl. No. 13/768,765 dated Mar. 17, 2015.
Interview Summary from the U.S. Patent and Trademark Office for U.S. Appl. No. 13/768,765 dated Jun. 11, 2015.
Examiner-Initiated Interview Summary from the U.S. Patent and Trademark Office for U.S. Appl. No. 13/768,765 dated Aug. 28, 2015 (1 page).
Notice of Allowance from the U.S. Patent and Trademark Office for U.S. Appl. No. 13/768,765 dated Aug. 28, 2015.
Notice of Allowance from the U.S. Patent and Trademark Office for U.S. Appl. No. 13/768,765 dated Nov. 20, 2015.
Notice of Allowance from the U.S. Patent and Trademark Office for U.S. Appl. No. 13/768,765 dated Jul. 28, 2016.
Non-Final Office Action from the U.S. Patent and Trademark Office for U.S. Appl. No. 13/907,128 dated Aug. 23, 2013 (9 pages).
Final Office Action from the U.S. Patent and Trademark Office for Application No. 13/907,128 dated Oct. 9, 2013 (19 pages).

(56) References Cited

OTHER PUBLICATIONS

Interview Summary from the U.S. Patent and Trademark Office for U.S. Appl. No. 13/907,128 dated Nov. 22, 2013 (3 pages).
Advisory Action from the U.S. Patent and Trademark Office for U.S. Appl. No. 13/907,128 dated Dec. 13, 2013 (2 pages).
Notice of Allowance from the U.S. Patent and Trademark Office for U.S. Appl. No. 13/907,128 dated Jan. 31, 2014 (10 pages).
Office Action from the U.S. Patent and Trademark Office for U.S. Appl. No. 14/043,165 dated Oct. 14, 2014.
Final Office Action from the U.S. Patent and Trademark Office for U.S. Appl. No. 14/043,165 dated Apr. 1, 2015.
Advisory Action from the U.S. Patent and Trademark Office for U.S. Appl. No. 14/043,165 dated Jul. 9, 2015 (3 pages).
Office Action from the U.S. Patent and Trademark Office for U.S. Appl. No. 14/043,165 dated Oct. 2, 2015.
Interview Summary from the U.S. Patent and Trademark Office for U.S. Appl. No. 14/043,165 dated. Dec. 21, 2015.
Final Office Action from the U.S. Patent and Trademark Office for U.S. Appl. No. 14/043,165 dated Feb. 17, 2016.
Appeal Brief from the U.S. Patent and Trademark Office for U.S. Appl. No. 14/043,165 dated Jul. 15, 2016.
Examiner's Answer to Appeal Brief from the U.S. Patent and Trademark Office for U.S. Appl. No. 14/043,165 dated Nov. 14, 2016 (13 pages).
Patent Board Decision from the U.S. Patent and Trademark Office for U.S. Appl. No. 14/043,165 dated Dec. 20, 2017 (11 page).
Notice of Allowance from the U.S. Patent and Trademark Office for U.S. Appl. No. 14/043,165 dated Mar. 19, 2018 (11 pages).
Notice of Allowance from the U.S. Patent and Trademark Office for U.S. Appl. No. 14/043,165 dated Aug. 6, 2018 (11 pages).
Non-Final Office Action from the U.S. Patent and Trademark Office for U.S. Appl. No. 14/081,225 dated Mar. 10, 2016 (23 pages).
Notice of Allowance from the U.S. Patent and Trademark Office for U.S. Appl. No. 14/081,225 dated Sep. 2, 2016 (11 pages).
Notice of Allowance from the U.S. Patent and Trademark Office for U.S. Appl. No. 14/081,225 dated Oct. 21, 2016 (2 pages).
Non-Final Office Action from the U.S. Patent and Trademark Office for U.S. Appl. No. 14/095,123 dated Mar. 3, 2015 (15 pages).
Applicant-Initiated Interview Summary from the U.S. Patent and Trademark Office for U.S. Appl. No. 14/095,123 dated May 1, 2015 (3 page).
Final Office Action from the U.S. Patent and Trademark Office for U.S. Appl. No. 14/095,123 dated Jul. 23, 2015 (13 pages).
Applicant-Initiated Interview Summary from the U.S. Patent and Trademark Office for U.S. Appl. No. 14/095,123 dated Aug. 27, 2015 (3 page).
Non-Final Office Action from the U.S. Patent and Trademark Office for U.S. Appl. No. 14/095,123 dated Feb. 23, 2016 (14 pages).
Final Office Action from the U.S. Patent and Trademark Office for U.S. Appl. No. 14/095,123 dated Jul. 20, 2016 (15 pages).
Notice of Allowance from the U.S. Patent and Trademark Office for U.S. Appl. No. 14/095,123 dated Mar. 30, 2017 (10 pages).
Restriction Requirement from the U.S. Patent and Trademark Office for U.S. Appl. No. 14/139,068 dated Jul. 28, 2015.
Office Action from the U.S. Patent and Trademark Office for U.S. Appl. No. 14/139,068 dated Mar. 11, 2016.
Notice of Allowance from the U.S. Patent and Trademark Office for U.S. Appl. No. 14/139,068 dated Sep. 21, 2016.
Office Action from the U.S. Patent and Trademark Office for U.S. Appl. No. 14/179,328 dated Sep. 11, 2014.
Applicant-Initiated Interview Summary from the U.S. Patent and Trademark Office for U.S. Appl. No. 14/179,328 dated Dec. 11, 2014 (3 pages).
Notice of Allowance from the U.S. Patent and Trademark Office for U.S. Appl. No. 14/179,328 dated Jan. 14, 2015.
Non-Final Office Action from the U.S. Patent and Trademark Office for U.S. Appl. No. 14/244,431 dated Mar. 18, 2016 (15 pages).
Applicant-Initiated Interview Summary from the U.S. Patent and Trademark Office for U.S. Appl. No. 14/244,431 dated Jun. 17, 2016 (3 pages).
Notice of Allowance from the U.S. Patent and Trademark Office for U.S. Appl. No. 14/244,431 dated Aug. 18, 2016 (8 pages).
Notice of Allowance from the U.S. Patent and Trademark Office for U.S. Appl. No. 14/244,431 dated Nov. 16, 2016 (4 pages).
Office Action from the U.S. Patent and Trademark Office for U.S. Appl. No. 14/298,806 dated Dec. 29, 2014 (15 pages).
Interview Summary from the U.S. Patent and Trademark Office for U.S. Appl. No. 14/298,806 dated Mar. 2, 2015 (3 pages).
Final Office Action from the U.S. Patent and Trademark Office for U.S. Appl. No. 14/298,806 dated Jun. 17, 2015 (20 pages).
Office Action from the U.S. Patent and Trademark Office for U.S. Appl. No. 14/298,806 dated Feb. 16, 2016 (16 pages).
Final Office Action from the U.S. Patent and Trademark Office for U.S. Appl. No. 14/298,806 dated Jul. 21, 2016.
Notice of Allowance from the U.S. Patent and Trademark Office for U.S. Appl. No. 14/298,806 dated Apr. 12, 2017 (10 pages).
Non-Final Office Action from the U.S. Patent and Trademark Office for U.S. Appl. No. 14/502,055 dated Jan. 20, 2016 (9 pages).
Applicant-Initiated Interview Summery from the U.S. Patent and Trademark Office for U.S. Appl. No. 14/502,055 dated Apr. 14, 2016 (3 pages).
Notice of Allowance from the U.S. Patent and Trademark Office for U.S. Appl. No. 14/502,055 dated Jun. 2, 2016 (10 pages).
Notice of Allowance from the U.S. Patent and Trademark Office for U.S. Appl. No. 14/502,055 dated Jun. 27, 2016 (2 pages).
Notice of Allowance from the U.S. Patent and Trademark Office for U.S. Appl. No. 14/502,055 dated Jul. 14, 2016 (2 pages).
Notice of Allowance from the U.S. Patent and Trademark Office for U.S. Appl. No. 14/502,055 dated Sep. 19, 2016 (3 pages).
Non-Final Office Action from the U.S. Patent and Trademark Office for U.S. Appl. No. 14/540,830 dated Jan. 17, 2017 (26 pages).
Applicant-Initiated Interview Summary from the U.S. Patent and Trademark Office for U.S. Appl. No. 14/540,830 dated Mar. 24, 2017 (3 pages).
Final Office Action from the U.S. Patent and Trademark Office for U.S. Appl. No. 14/540,830 dated May 15, 2017 (42 pages).
Applicant-Initiated Interview Summary from the U.S. Patent and Trademark Office for U.S. Appl. No. 14/540,830 dated Jul. 28, 2017 (3 page).
Notice of Allowance from the U.S. Patent and Trademark Office for U.S. Appl. No. 14/540,830 dated Aug. 15, 2017 (8 pages).
Office Action from the U.S. Patent and Trademark Office for U.S. Appl. No. 14/687,853 dated Aug. 13, 2015.
Notice of Allowance from the U.S. Patent and Trademark Office for U.S. Appl. No. 14/687,853 dated Feb. 25, 2016.
Notice of Allowance from the U.S. Patent and Trademark Office for U.S. Appl. No. 14/687,853 dated Jun. 2, 2016.
Non-Final Office Action from the U.S. Patent and Trademark Office for U.S. Appl. No. 14/792,210 dated Aug. 27, 2018 (53 pages).
Final Office Action from the U.S. Patent and Trademark Office for U.S. Appl. No. 14/792,210 dated Mar. 5, 2019 (17 pages).
Notice of Allowance from the U.S. Patent and Trademark Office for U.S. Appl. No. 14/792,210 dated Jun. 17, 2019 (10 pages).
Notice of Allowance from the U.S. Patent and Trademark Office for U.S. Appl. No. 14/792,210 dated Sep. 5, 2019 (2 pages).
Notice of Allowance from the U.S. Patent and Trademark Office for U.S. Appl. No. 14/792,210 dated Oct. 11, 2019 (9 pages).
Non-Final Office Action from the U.S. Patent and Trademark Office for U.S. Appl. No. 15/140,346 dated May 28, 2019 (39 pages).
Final Office Action from the U.S. Patent and Trademark Office for U.S. Appl. No. 15/140,346 dated Oct. 31, 2019 (41 pages).
Non-Final Office Action from the U.S. Patent and Trademark Office for U.S. Appl. No. 15/140,348 dated Nov. 19, 2018 (33 pages).
Non-Final Office Action from the U.S. Patent and Trademark Office for U.S. Appl. No. 15/140,348 dated Jul. 9, 2019 (21 pages).
Non-Final Office Action from the U.S. Patent and Trademark Office for U.S. Appl. No. 15/140,348 dated Dec. 4, 2019 (21 pages).
Final Office Action from the U.S. Patent and Trademark Office for U.S. Appl. No. 15/140,348 dated Jun. 11, 2020 (27 pages).
Non-Final Office Action from the U.S. Patent and Trademark Office for U.S. Appl. No. 15/140,351 dated Jul. 30, 2018 (25 pages).
Final Office Action from the U.S. Patent and Trademark Office for U.S. Appl. No. 15/140,351 dated Dec. 6, 2018 (21 pages).

(56) References Cited

OTHER PUBLICATIONS

Advisory Action from the U.S. Patent and Trademark Office for U.S. Appl. No. 15/140,351 dated Mar. 5, 2019 (4 pages).
Examiner-Initiated Interview Summary from the U.S. Patent and Trademark Office for U.S. Appl. No. 15/140,351 dated Mar. 5, 2019 (2 pages).
Non-Final Office Action from the U.S. Patent and Trademark Office for U.S. Appl. No. 15/140,351 dated May 21, 2019 (14 pages).
Applicant-Initiated Interview Summary from the U.S. Patent and Trademark Office for U.S. Appl. No. 15/140,351 dated Jul. 15, 2019 (3 pages).
Final Office Action from the U.S. Patent and Trademark Office for U.S. Appl. No. 15/140,351 dated Nov. 14, 2019 (14 pages).
Notice of Allowance from the U.S. Patent and Trademark Office for U.S. Appl. No. 15/140,351 dated Mar. 5, 2020 (16 pages).
Examiner-Initiated Interview Summary from the U.S. Patent and Trademark Office for U.S. Appl. No. 15/140,351 dated Mar. 5, 2020 (1 pages).
Non-Final Office Action from the U.S. Patent and Trademark Office for U.S. Appl. No. 15/140,363 dated Jun. 3, 2019 (33 pages).
Notice of Allowance from the U.S. Patent and Trademark Office for U.S. Appl. No. 15/163,600 dated Aug. 11, 2016.
Notice of Allowance from the U.S. Patent and Trademark Offoce for U.S. Appl. No. 15/163,600 dated Sep. 14, 2016 (6 pages).
Examiner-Initiated Interview Summary from the U.S. Patent and Trademark Office for U.S. Appl. No. 15/163,600 dated Sep. 14, 2016 (1 page).
Non-Final Office Action from the U.S. Patent and Trademark Office for U.S. Appl. No. 15/188,819 dated Jul. 3, 2018 (7 pages).
Applicant-Initiated Interview Summary from the U.S. Patent and Trademark Office for U.S. Appl. No. 15/188,819 dated Sep. 24, 2018 (4 pages).
Notice of Allowance from the U.S. Patent and Trademark Office for U.S. Appl. No. 15/188,819 dated Jan. 25, 2019 (7 pages).
Notice of Allowance from the U.S. Patent and Trademark Office for U.S. Appl. No. 15/188,819 dated Mar. 15, 2019 (5 pages).
Notice of Allowance from the U.S. Patent and Trademark Office for U.S. Appl. No. 15/188,819 dated Aug. 21, 2019 (8 pages).
Notice of Allowance from the U.S. Patent and Trademark Office for U.S. Appl. No. 15/188,819 dated Oct. 2, 2019 (4 pages).
Notice of Allowance from the U.S. Patent and Trademark Office for U.S. Appl. No. 15/188,819 dated Jan. 24, 2020 (8 pages).
Notice of Allowance from the U.S. Patent and Trademark Office for U.S. Appl. No. 15/188,819 dated Mar. 20, 2020 (4 pages).
Non-Final Office Action from the U.S. Patent and Trademark Office for U.S. Appl. No. 15/188,872 dated Oct. 19, 2018 (12 pages).
Final Office Action from the U.S. Patent and Trademark Office for U.S. Appl. No. 15/188,872 dated May 8, 2019 (14 pages).
Applicant-Initiated Interview Summary from the U.S. Patent and Trademark Office for U.S. Appl. No. 15/188,872 dated Jul. 15, 2019 (4 pages).
Notice of Allowance from the U.S. Patent and Trademark Office for U.S. Appl. No. 15/188,872 dated Aug. 23, 2019 (10 pages).
Notice of Allowance from the U.S. Patent and Trademark Office for U.S. Appl. No. 15/188,872 dated Oct. 28, 2019 (5 pages).
Notice of Allowance from the U.S. Patent and Trademark Office for U.S. Appl. No. 15/188,872 dated Jan. 23, 2020 (9 pages).
Notice of Allowance from the U.S. Patent and Trademark Office for U.S. Appl. No. 15/188,872 dated Mar. 20, 2020 (5 pages).
Non-Final Office Action from the U.S. Patent and Trademark Office for U.S. Appl. No. 15/254,627 dated Dec. 12, 2016 (12 pages).
Notice of Allowance from the U.S. Patent and Trademark Office for U.S. Appl. No. 15/254,627 dated Apr. 3, 2017 (11 pages).
Notice of Allowance from the U.S. Patent and Trademark Office for U.S. Appl. No. 15/254,627 dated Jul. 13, 2017 (4 pages).
Non-Final Office Action from the U.S. Patent and Trademark Office for U.S. Appl. No. 15/292,006 dated May 9, 2018 (17 pages).
Final Office Action from the U.S. Patent and Trademark Office for U.S. Appl. No. 15/292,006 dated Oct. 17, 2018 (18 pages).
Examiner-Initiated Interview Summary from the U.S. Patent and Trademark Office for U.S. Appl. No. 15/292,006 dated Nov. 29, 2018 (1 page).
Notice of Allowance from the U.S. Patent and Trademark Office for U.S. Appl. No. 15/292,006 dated Nov. 29, 2018 (12 pages).
Notice of Allowance from the U.S. Patent and Trademark Office for U.S. Appl. No. 15/292,006 dated Jan. 28, 2019 (3 pages).
Notice of Allowance from the U.S. Patent and Trademark Office for U.S. Appl. No. 15/292,006 dated Apr. 10, 2019 (6 pages).
Notice of Allowance from the U.S. Patent and Trademark Office for U.S. Appl. No. 15/292,006 dated Aug. 7, 2019 (6 pages).
Notice of Allowance from the U.S. Patent and Trademark Office for U.S. Appl. No. 15/292,006 dated Aug. 22, 2019 (3 pages).
Notice of Allowance from the U.S. Patent and Trademark Office for U.S. Appl. No. 15/292,006 dated Sep. 4, 2019 (7 pages).
Notice of Allowance from the U.S. Patent and Trademark Office for U.S. Appl. No. 15/292,006 dated Oct. 29, 2019 (6 pages).
Notice of Allowance from the U.S. Patent and Trademark Office for U.S. Appl. No. 15/292,006 dated Dec. 12, 2019 (3 pages).
Notice of Allowance for U.S. Appl. No. 15/292,006 dated Feb. 10, 2020 (3 pages).
Non-Final Office Action from the U.S. Patent and Trademark Office for U.S. Appl. No. 15/292,014 dated Jan. 24, 2019 (7 pages).
Notice of Allowance from the U.S. Patent and Trademark Office for U.S. Appl. No. 15/292,014 dated Jul. 11, 2019 (8 pages).
Notice of Allowance from the U.S. Patent and Trademark Office for U.S. Appl. No. 15/292,014 dated Nov. 15, 2019 (7 pages).
Notice of Allowance from the U.S. Patent and Trademark Office for U.S. Appl. No. 15/292,014 dated Dec. 5, 2019 (4 pages).
Notice of Allowance from the U.S. Patent and Trademark Office for U.S. Appl. No. 15/292,014 dated Jan. 8, 2020 (4 pages).
Notice of Allowance from the U.S. Patent and Trademark Office for U.S. Appl. No. 15/292,014 dated Jan. 23, 2020 (4 pages).
Office Action from the U.S. Patent and Trademark Office for U.S. Appl. No. 15/292,023 dated Jan. 12, 2017.
Notice of Allowance from the U.S. Patent and Trademark Office for U.S. Appl. No. 15/292,023 dated Apr. 11, 2017 (11 pages).
Non-Final Office Action from the U.S. Patent and Trademark Office for U.S. Appl. No. 15/346,530 dated Mar. 26, 2018 (12 pages).
Applicant-Initiated Interview Summary from the U.S. Patent and Trademark Office for U.S. Appl. No. 15/346,530 dated May 17, 2018 (3 pages).
Final Office Action from the U.S. Patent and Trademark Office for U.S. Appl. No. 15/346,530 dated Sep. 6, 2018 (14 pages).
Advisory Action from the U.S. Patent and Trademark Office for U.S. Appl. No. 15/346,530 dated Nov. 21, 2018 (4 pages).
Notice of Allowance from the U.S. Patent and Trademark Office for U.S. Appl. No. 15/346,530 dated May 15, 2019 (8 pages).
Notice of Allowance from the U.S. Patent and Trademark Office for U.S. Appl. No. 15/346,530 dated Aug. 27, 2019 (7 pages).
Notice of Allowance from the U.S. Patent and Trademark Office for U.S. Appl. No. 15/346,530 dated Oct. 9, 2019 (4 pages).
Notice of Allowance from the U.S. Patent and Trademark Office for U.S. Appl. No. 15/346,530 dated Dec. 17, 2019 (4 pages).
AGFA HealthCare, color brochure "IMPAX 6: Digital Image and Information Management," © 2012 Agfa Healthcare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US) 2012. © 2012 Agfa HealthCare N.V. Downloaded from http://www.agfahealthcare/en/he/library/libraryopen?ID=37459801. Accessed on Feb. 9, 2015.
AMD Technologies, Inc. Catella PACS 5.0 Viewer User Manual (112 pgs), © 2010, AMD Technologies, Inc. (Doc. 340-3-503 Rev. 01), Downloaded from http://www.amdtechnologies.com/lit/cat5viewer.pdf . . . Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/Product Brochures/MR-5032Rev.%204interWORKS%20RISPACSPackage.pdf. Accessed on Feb. 9, 2015.
Bergstrom, Patrik. "Automated setup of display protocols" (2015).

(56) References Cited

OTHER PUBLICATIONS

BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS) © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
Candelis, ImageGridTM: Image Management Appliance, 6 page color brochure. (AD-012 Rev. F Nov. 2012). © Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brocure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cemer, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an information-processing Study, Jan. 2003, Journal of the American medical informatics Association, vol. 10, No. 1, pp. 39-51.
DR Systems DominatorTM Guide for Reading Physicians, Release 8.2. 546 pages, (TCP-000260-A), © 1997-2009, DR Systems, Inc. Downloaded from https://resources,dominator.com/assets/004/6999.pdf. Document accessed on Feb. 9, 2015.
DR Systems, DR Scheduler User Guide, Release 8.2, 410 pages (TCP-000115-A), © 1997-2009, DR Systems, Inc. Downloaded from https://resources.dominator,com/assets/003/6850.pdf. Document accessed Feb. 9, 2015.
Erickson, et al.: "Effect of Automated Image Registration on Radiologist Interpretation," Journal of Digital Imaging, vol. 20, No. 2 (Jun. 2007); pp. 105-113.
Erickson, et al.: "Image Registration Improves Confidence and Accuracy of Image Interpretation," Special Issue-Imaging Informatics, Cancer Informatics 2007: 1 19-24.
FUJIFILM Medical Systems, Synapse ® Product Data, Synapse Release Version 3.2.1, Foundation Technologies, 4 page color brochure, (XBUSSY084) Aug. 2008., Downloaded from http://www.fujifilmusa.com/shared/bin/foundation/pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008., Downloaded from http:www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure (XBUSSY082) Aug. 2008., Downloaded rom http://www.fujifilmusa.com/share/bin/workstation.pdf. Accessed on Feb. 9, 2015.
GE Healthcare, Centricity PACS, in 8 page printout. Accessed at http://www.gehealthcare.com/en/products/categories/healthcare_it/medical_imagining-informatics_-_ris-pacs-cvis/centricity_pacs. Accessed on Feb. 9, 2015.
Handlylife.com—Features of Handy Patients Enterprise, in 4 page printout. Accessed from http://www.handylife.com/en/software/features.html. Accessed on Feb. 18, 2015.
Handylife.com—Overview of Handy Patients Enterprise, in 2 page printout. Accessed from http://www.handylife.com/en/software/overview.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See The Future, in 12 pages, color brochure, (BR080809AUS) © 2009 iCRco.ClarityPACS. Downloaded from http://www.claritypacs.com/pdfs/ISeeFuture_26Web.pclf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#lproducts-services/ctnu. Accessed on Feb. 9, 2015.
Infinitt, PACS, RIS Mammo PACS, Cariology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incorporated. Downloaded http://www.intelerad.com/wp-content/uploads/sites/2/2014/08/IntelPACS-brocure.pdf. Accessed on Feb. 9, 2015.
Intelerad, InteleViewer, 2 page color brochure, © 2014 Intelerad Medical Systems Incorporated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded form http://www.intuitiveimaging.com/2013/pdf/ImageQube%20one-sheet.pdf. Accessed on Feb. 9, 2015.
Ivetic, D.., and Dragan, D., Medical Image on the Go!, 2009, J Med Syst, vol. 35, pp. 499-516.
Kuhl, Helen: Comparison Chart/PACS, Customers Are Happy, But Looking for More, (color) Imaging Technology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS, 5.0 Web Viewer, Cariopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/poviders/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure © 2006-2014 Medweb. Downloaded from http://www.medweb.com/docs/rispacs_brochure_2014.pdf. Accessed on Feb. 9, 2015.
Mendelson, et al., "informatics in Radiology—Image Exchange: IHE and the Evolution of Image Sharing," RadioGraphics, Nov.-Dec. 2008, Vo. 28, No. 7.
Merge Radiology Solutions, Merge PACS, A real-time picture archiving communication system, (PAX-21990 rev 2.0) 2 page color brochure. Downloaded from http:/www.merge.com/MergeHealthcare/media/documents/brocures/Merge_PACS_web.pdf. Accessed on Feb. 9, 2015.
NOVARAD Enterprise Imaging Solutions, NOVAPACS, 2 page (color) printout. Accessed at http://www.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/producst_01.html. Accessed on Feb. 9, 2015.

(56) References Cited

OTHER PUBLICATIONS

Philips IntelliSpace PACS, in 2 color page printout. Accessed at http://www.healthcare.philips.com/main/products/healthcare_informatics/products/enterprise_ imaging_informatics/isite_pacs. Accessed on Feb. 9, 2015.
Philips, IntelliSpace; Multi-modality tumor tracking application versus manual PACS methods, A time study for Response Evaluation Criteria in Solid Tumors (RECIST). 2012, Koninkliijke Philips Electronics N.V., in four pages.
Radcliffe, et al., "Comparison of Stereo Disc Photographs and Alternation Flicker Using a Novel Matching Technology for Detecting Glaucoma Progression", Ophthalmic Surgery, Lasers & Imaging, Jun. 9, 2010.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Rosset et al.: OsiriX: An Open-Source Software for Navigating in Multidimensional DICOM Images, Journal of digital Imaging, Sep. 2004, pp. 205-216.
Sage Intergy PACS | Product Summary. Enhancing Your Workflow by Delivering Web-based Diagnostic Images When and Where You Need them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Sandberg et al., "Automatic detection and notification of "wrong patient-wrong location" errors in the operatin room," Surgical Innovation, Sep. 2005, vol. 12, No. 3, pp. 253-260.
Schellingerhout, Dawid, MD, et al.: "Coregistration of Head CT Comparison Studies: Assessment of Clinical Utility," Acad Radiol 2003; 10:242-248.
Scimage, Cardiology PACS, in 8 color pagge printout. Accessed at http://www.scimage.com/solutions/clinical-solutions/cardiology. Accessed on Feb. 9, 2015.
Sectra RIS PACS, in 2 color page printout. Accessed at http://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaginig-it/imagining-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Sprawls, "Image Characteristics and Quality," Physical Principles of Medical Imaging, http://www.sprawls.org/resources pp. 1-14.
Stryker, Imaging—OfficePACS Power Digital Imaging, in one color page printout. http://www.stryker.com/emea/Solutions/Imaging/OfficePACSPowerDigitalImaging/index.htm. Accessed on Feb. 9, 2015.
Stryker, Office PACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
Syed, et al., "Automated alternation flicker for the detection of optic disc haemorrhages", ACTA Ophthalmologica 2012, accepted for publication on Nov. 26, 2010.
Syed, et al., "Detection of Progressive Glaucomatous Optic Neuropathy Using Automated Alternation Flicker With Stereophotography," Research Letter, Arch Ophthalmol, published online Dec. 13, 2010. 2010 American Medical Association.
Tahmoush, D. and Samet, H., A New Database for Medical Images and Information, 2007, Medical Imaging 2007; PACS and Imaging Informatics, vol. 6516, pp. 1-9.
Tay, et al., "Assessing Signal Intensity Change on Well-registered Images: Comparing Subtraction, Color-encoded Subtraction, and Parallel Display Formats", Original Research: Computer Applications Radiology, vol. 260: No. 2—Aug. 2011.
TeraRecon iNtuition—Workflow <www.terarecon.com/wordpress/our-solutions/intuition-workflow> Last accessed Nov. 8, 2013, 2 pages.
TeraRecon iNtuition pamphlet in 20 pages, retrieved on Nov. 8, 2013, available at http://int.terarecon.com/wp-content/uploads/2013/11/brochure_english2013.pdf.
UltraRAD—ultra VISION, 1 page (color) Downloaded from http://www.ultraradcorp.com/pdf/UltraVISION.pdf. Accessed on Feb. 9, 2015.
VanderBeek, et al., "Comparing the detection and agreement of parapapillary atrophy progression using digital optic disk photographs and alternation flicker", Glaucoma, Graefes Arch Clin Exp Ophthalmol (2010) 248:1313-1317, Apr. 15, 2010.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vistek Opal-RAD, 4 color page printout. Accessed at http://vistek.net/products/opal-rad. Accessed on Feb. 9, 2015.
Voyager Imaging—Voyager PACS Radiologist Workstation, 2 page color brochure. Downloaded from http://www.intellirad.com/au/assets/Uploads/Voyager-PacsWorkstations.pdf? Accessed on Feb. 9, 2015.
Voyager Imaging—Voyager PACS, 3 page color brochure. Downloaded from http://www.intellirad.com/au/index.php/assets/Uploads/Voyager-Pacs3.pdf. Accessed on Feb. 9, 2015.
Notice of Allowance from the U.S. Patent and Trademark Office for U.S. Appl. No. 15/140,348 dated Sep. 3, 2020 (8 pages).
Notice of Allowance from the U.S. Patent and Trademark Office for U.S. Appl. No. 15/140,348 dated Oct. 15, 2026 (8 pages).
Notice of Allowance from the U.S. Patent and Trademark Office for U.S. Appl. No. 15/140,351 dated Sep. 22, 2020 (8 pages).
Notice of Allowance from the U.S. Patent and Trademark Office for U.S. Appl. No. 15/140,351 dated Oct. 19, 2026 (2 pages).
Final Office Action from the U.S. Patent and Trademark Office for U.S. Appl. No. 15/140,363 dated Mar. 23, 2021 (27 pages).
Henri et al., "Design and Implementation of World Wide Web-Based Tools For Image Management in Computed Tomography, Magnetic Resonance Imaging, and Ultrasonography" (pp. 77-79) (Year: 1997).
Brown et al., "Standardisation in medical image management" (pp. 227-238) (Year: 1998).
Osteaux et al., "Picture archiving and communication system (PACS): a progressive approach with small systems" (pp. 166-174) (Year: 1996).
Non-Final Office Action from the U.S. Patent and Trademark Office for U.S. Appl. No. 16/692,283 dated May 13, 2021 (7 pages).

* cited by examiner

| Modality | Exam | CAP | Rule to run CAP |
|---|---|---|---|
| CT | chest | spine fracture dection | (clinical indication is "trauma" or "pain" or "history of fracture") and approved by insurance |
| CT | chest | lung nodule detection | always |
| CT | chest | lung parenchyma analysis | on-demand per radiologist |
| CT | abdomen | spine fracture dection | (clinical indication is "trauma" or "pain" or "history of fracture") and approved by insurance |
| CT | abdomen | liver analysis (mass/volume/density) | when ordered by referring physician |
| CT | thoracic spine | spine fracture dection | always |
| CT | lumbar spine | spine fracture dection | always |
| CT | brain perfusion | CT brain perfusion analysis | always |
| MRI | brain with contrast | MRI brain tumor size | tumor |
| MRI | brain with contrast | MRI brain tumor change detection | tumor and prior exam |
| MRI | brain perfusion | MRI brain perfusion analysis | always |
| MRI | brain | MRI brain volumetric analysis | "dementia" |
| MRI | brain | MRI brain CSF analysis | "hydrocephalus" or abnormal brain volumetric analysis |
| MRI | brain MRA | MRA brain aneurysm detection CAD | always |
| CT | brain CTA | 3D Vessel tracking | on-demand |
| CT | brain CTA | Brain vessel stenosis CAD | on demand (automatically run 3D Vessel tracking first) |
| CT | brain CTA | Brain aneurysm detection CAD | on demand (automatically run 3D Vessel tracking first) |

Fig. 4A

Computerized Advanced Processing Rules

IF ((imaging exam is CT of Chest) and (clinical indication includes "trauma") and (approved by insurance)) THEN run (spine fracture dection CAD)

IF ((imaging exam is CT of Chest) THEN run(lung nodule detection CAD)

IF ((imaging exam is CT of Abdomen) and (clinical indication includes "trauma") and (approved by insurance)) THEN run (spine fracture dection CAD)

IF ((imaging exam is CT of Thoracic Spine) THEN run (spine fracture detetion CAD)

IF ((imaging exam is MRI of brain) and (clinical indication includes "dementia")) THEN run (MRI brain volumetric analysis processing)

IF ((imaging exam is MRI of brain) and ((clinical indication includes "hydrocephalus") or (MRI Brain volume analysis is abnormal))) THEN run (MRI CSF analysis processing)

IF (imaging exam is MRA of brain) THEN run (MRA brain aneurysm detection CAD)

IF ((imaging exam is CTA of Brain) and (clinical indication includes stroke)) THEN run (3D Vessel Tracking)
    and THEN run(Brain vessel stenosis CAD) and THEN run(Brain aneurysm detection CAD)

Fig. 4B

| Name | Number | Date | Time | Mod | Exam Description | CAP/CAD/Processing |
|---|---|---|---|---|---|---|
| Adler, Marry | 1029987 | 11/15/2011 | 7:30 | MRI | Brain W/ Contrast | pending: Brain Metastasis CAD |
| Carter, Carl | 1073322 | 11/15/2011 | 11:45 | MRI | Brain W/ Perfusion | pending: Perfusion Processing |
| Smith, John | 1093345 | 11/15/2011 | 8:00 | MRI | Brain W/O Contrast | complete: Brain Volumetric analysis |
| | | | | | | in progress: Brain CSF analysis |
| Swanson, Carl | 1098833 | 11/15/2011 | 9:00 | MRI | Brain W/ Contrast | in progress: 3D registration vs 10/1/2011 |
| | | | | | | pending: change detection vs 10/1/2011 |
| Torran, Barry | 1023486 | 11/15/2011 | 9:15 | CTA | Circle of Willis | complete: Aneurysm CAD |

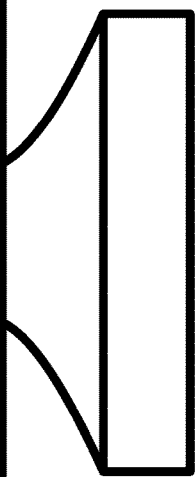

Fig. 5

INTELLIGENT MANAGEMENT OF COMPUTERIZED ADVANCED PROCESSING

CROSS-REFERENCE TO RELATED APPLICATION

This application is a divisional of U.S. patent application Ser. No. 15/188,872, filed Jun. 21, 2016, which is a divisional of U.S. patent application Ser. No. 14/139,068, filed Dec. 23, 2013, which claims the benefit of priority under 35 U.S.C. § 119(e) of U.S. Provisional Application No. 61/750,662, filed Jan. 9, 2013, the disclosures of which are hereby incorporated by reference herein in their entireties.

BACKGROUND

In medical imaging, some exams are processed using computerized advanced processing, such as Computer Aided Diagnosis (CAD) systems, quantitative analysis (blood flow, volumetrics, image enhancement, etc.), or other processing systems, for example. With continued progress in the fields of Artificial Intelligence, image processing, and image analysis, it is anticipated that the use of CAD and advanced processing will grow over time and their use will become routine in the future.

SUMMARY

The systems, methods, and devices described herein each have several aspects, no single one of which is solely responsible for its desirable attributes. Without limiting the scope of this disclosure, several non-limiting features will now be described briefly.

According to an embodiment, a computing system is disclosed that comprises: one or more hardware computer processors configured to execute software instructions; and one or more electronic storage devices in communication with the one or more hardware computer processors and storing software modules, the software modules comprising software instructions configured for execution by the one or more hardware computer processors in order to cause the computing system to: access, from one or more image storage devices, an image series comprising one or more medical images; determine an exam characteristic associated with the image series, the exam characteristic including a result of a previously run computerized advanced processing technique; access, from a computerized advanced processing data structure, rules for execution of respective computerized advanced processing techniques, the rules indicating: one or more associations between exam characteristics and corresponding computerized advanced processing techniques, the exam characteristics including at least a modality and exam type; and one or more criteria associated with respective computerized advanced processing techniques for automatically initiating execution of corresponding computerized advanced processing techniques; determine, based on the rules, one or more computerized advanced processing techniques associated with the determined exam characteristic of the image series; and for each of the determined computerized advanced processing techniques: in response to determining that criteria associated with the computerized advanced processing technique are satisfied, automatically initiate execution of the computerized advanced processing technique on the image series.

According to another embodiment, a computing system is disclosed that comprises: one or more hardware computer processors configured to execute software instructions; and one or more electronic storage devices in communication with the one or more hardware computer processors and storing software modules, the software modules comprising software instructions configured for execution by the one or more hardware computer processors in order to cause the computing system to: access, from one or more image storage devices, an image series comprising one or more medical images; determine an exam characteristic associated with the image series; access a computerized advanced processing data structure including rules for executing respective computerized advanced processing techniques based on corresponding exam characteristics; identify one or more rules that are matched by the exam characteristic; and initiate execution of computerized advanced processing techniques associated with the identified one or more rules that are matched by the exam characteristic.

According to yet another embodiment, a computing system is disclosed that comprises: one or more hardware computer processors configured to execute software instructions; and one or more electronic storage devices in communication with the one or more hardware computer processors and storing software modules, the software modules comprising software instructions configured for execution by the one or more hardware computer processors in order to cause the computing system to: access, from one or more image storage devices, one or more image series each comprising one or more medical images; access a computerized advanced processing data structure including rules indicating respective computerized advanced processing techniques available for respective subsets of characteristics associated with medical data; identify one or more rules that are matched by characteristics of a particular one or more image series; and generate a user interface for display to a user, the user interface including information regarding computerized advanced processing techniques associated with the identified one or more rules that are matched by characteristics of the particular one or more image series.

According to another embodiment, a computing system is disclosed that comprises: one or more hardware computer processors configured to execute software instructions; and one or more electronic storage devices in communication with the one or more hardware computer processors and storing software modules, the software modules comprising software instructions configured for execution by the one or more hardware computer processors in order to cause the computing system to: access, from one or more image storage devices, an image series comprising one or more medical images; determine a characteristic associated with a first computerized advanced processing technique applied to the image series; access a computerized advanced processing data structure including rules for executing computerized advanced processing techniques based on characteristics of previously applied computerized advanced processing techniques; identify a rule that corresponds to the determined characteristic associated with the first computerized advanced processing technique, the rule indicating execution of a second computerized advanced processing technique; and initiate application of the second computerized advanced processing technique to the image series.

BRIEF DESCRIPTION OF THE DRAWINGS

FIGS. 4A-4B are tables illustrating examples of rules that may be stored by systems of the present disclosure, according to various embodiments.

FIG. 5 illustrates an example user interface in which status information is displayed, according to an embodiment of the present disclosure.

DETAILED DESCRIPTION

Figure 1:
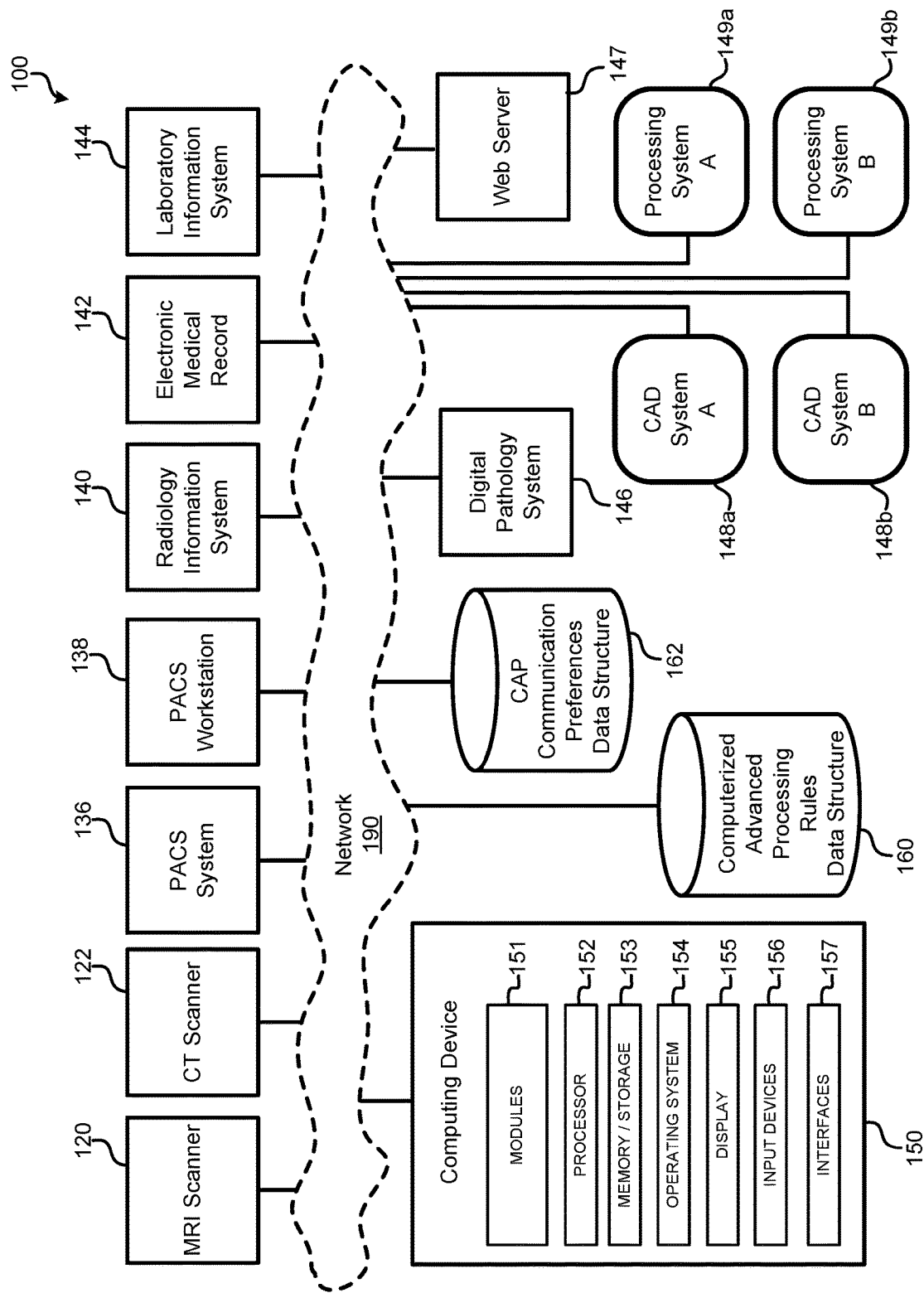
FIGS. 1, 2, and 3 are system and block diagrams which show various example components of systems and computing devices for implementing various methods and processes of the present disclosure, according to various embodiments.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

In various embodiments, systems and methods are disclosed for automatically managing how and when computerized advanced processing techniques (for example, CAD and/or other image processing) are used. In some embodiments, the systems and methods discussed herein allow users, such as radiologists, to efficiently interact with a wide variety of computerized advanced processing ("CAP") techniques using computing devices ranging from Picture Archiving and Communications System (PACS) workstations to handheld devices such as smartphone, tablets, or even smart watches. Furthermore, the systems and methods may, in various embodiments, automatically manage how data associated with these CAP techniques (for example, results of application of one or more computerized advanced processing techniques) are used, such as how data associated with the computerized analyses is reported, whether comparisons to prior abnormalities should be automatically initiated, whether the radiologist should be alerted of important findings, and the like.

In order to facilitate an understanding of the systems and methods discussed herein, certain terms may be defined in this document. Such terms should be construed to include the provided definitions, the ordinary and customary meaning of the terms, and/or any other implied meaning for the respective terms. Accordingly, any definitions provided herein do not limit the meaning of the defined terms, but only provide exemplary definitions.

The term CAP (computerized advanced processing), as use herein, should be interpreted to cover one or more of the various computerized image analyses, image analysis techniques, and/or image processing techniques discussed herein, and/or any similar computerized processing techniques that are currently or later available. CAP will be described herein with regard to radiology images, but CAP and the systems and methods described herein may be applied in other areas including, but not limited to, other types of medical images (for example, cardiology, dermatology, pathology and/or endoscopy, among others), computer generated images (for example, 3D images from virtual colonoscopy, 3D images of vessels from CTA, and the like), images from other fields (for example, surveillance imaging, satellite imaging, and the like), as well as non-imaging data including audio, text, and numeric data. In some embodiments, CAP may include, but is not limited to, volumetric rendering, multiplanar reconstruction (MPR), maximum intensity projection (MIP), other image processing techniques, and the like.

Example Computing Systems

FIG. 1 is a system diagram which shows the various components of a system 100 configured for managing and/or displaying information utilizing certain systems and methods described herein, according to various embodiments. As shown, the system 100 may include a computing device 150 and may further include other systems, such as those shown in FIG. 1 and described below.

The computing device 150, also referred to herein as "device 150," may take various forms. In one embodiment, the computing device 150 may be an information display computing device, and/or a computer workstation having information display software modules 151. In other embodiments, software modules 151 may reside on another computing device, such as a web server or other server, and a user directly interacts with a second computing device that is connected to the web server via a computer network.

In one embodiment, the computing device 150 comprises one or more computing devices, such as a server, a desktop computer, a workstation, a laptop computer, a mobile computer, a smartphone, a tablet computer, a cell phone, a personal digital assistant, a gaming system, a kiosk, an audio player, and/or any other device that utilizes a graphical user interface, such as office equipment, automobiles, airplane cockpits, household appliances, automated teller machines, self-service checkouts at stores, information and other kiosks, ticketing kiosks, vending machines, industrial equipment, and/or a television, for example.

The computing device 150 may run an off-the-shelf operating system 154 such as a Windows, Linux, MacOS, Android, or iOS. The computing device 150 may also run a more specialized operating system which may be designed for the specific tasks performed by the computing device 150.

The computing device 150 may include one or more computer processors 152, for example, hardware computer processors. The computer processors 152 may include central processing units (CPUs), and may further include dedicated processors such as graphics processor chips, or other specialized processors. The processors may be used to execute computer instructions based on the modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, Lua, C, C++, or C #. While "modules" are generally discussed herein with reference to software, any modules may alternatively be represented in hardware or firmware. In various embodiments, the modules described herein refer to logical modules that may be combined with other modules or divided into sub-modules despite their physical organization or storage.

The computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The computing device 150 may also include or be interfaced to one or more display devices 155 that provide information to users of the computing device. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The computing device 150 may also include or be interfaced to one or more input devices 156 which receive input from users, such as a keyboard, trackball, mouse, 3D mouse, drawing tablet, joystick, game controller, touch sensitive surface (for example, capacitive or resistive touch screen), touchpad, accelerometer, video camera and/or microphone.

The computing device 150 may also include one or more interfaces 157 which allow information exchange between computing device 150 and other computers and input/output devices using systems such as Ethernet, Wi-Fi, Bluetooth, as well as other wired and wireless data communications techniques.

The modules of the computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing device 150 may be combined into fewer components and modules or further separated into additional components and modules.

The computing device 150 may communicate and/or interface with other systems and/or devices. In one or more embodiments, the computer device 150 may be connected to a computer network 190. The computer network 190 may take various forms. For example, the computer network 190 may be a wired network or a wireless network, or it may be some combination of both. The computer network 190 may be a single computer network, or it may be a combination or collection of different networks and network protocols. Additionally, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanners 120. The MRI scanner 120 may be used to acquire MRI images from patients, and may share the acquired images with other devices on the network 190. The network 190 may also include one or more CT scanners 122. The CT scanners 122 may also be used to acquire images and, like the MRI scanner 120, may then store those images and/or share those images with other devices via the network 190. Any other scanner or device capable of inputting or generating information that can be presented to the user as images, graphics, text or sound may be connected to the network 190, including, for example, computing systems used in the fields of ultrasound, angiography, nuclear medicine, radiography, endoscopy, pathology, dermatology, and the like.

Also connected to the network 190 may be a Picture Archiving and Communications System (PACS) 136 and PACS workstation 138. The PACS System 136 may be used for the storage, retrieval, distribution and presentation of images (such as those created and/or generated by the MRI scanner 120 and CT Scanner 122). The medical images may be stored in an independent format, an open source format, or some other proprietary format. A common format for image storage in the PACS system is the Digital Imaging and Communications in Medicine (DICOM) format. In various embodiments, the stored images may be transmitted digitally via the PACS system, often reducing or eliminating the need for manually creating, filing, or transporting film jackets.

The network 190 may also be connected to a Radiology Information System (RIS) 140. In an embodiment, the radiology information system 140 may be a computerized system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a Laboratory Information System 144. In an embodiment, the Laboratory Information System 144 may be a software system which stores information created or generated by clinical laboratories. Also attached to the network 190 may be a Digital Pathology System 146 that may be used to digitally manage and store information related to medical pathology.

Also attached to the network 190 may be one or more Computer Aided Diagnosis Systems (CAD) systems 148 (including CAD systems 148a, 148b, and/or any quantity of CAD systems) that are generally used to perform CAP such as, for example, CAD processes. In one embodiment, the CAD systems 148 functionality may reside in a computing device separate from computing device 150 while in another embodiment the CAD systems 148 functionality may reside within computing device 150.

Also attached to the network 190 may be one or more Processing Systems 149 (including Processing Systems 149a, 149b, and/or any quantity of Processing Systems) that may be used to perform CAP such as, for example, computations on imaging information to create new views of the information, for example, 3D volumetric display, Multiplanar Reconstruction (MPR), and Maximum Intensity Projection reconstruction (MIP), as well as other types of processing, for example image enhancement, volume quantification, blood-flow quantification, and the like. In one embodiment, such processing functionality may reside in a computing device separate from computing device 150 while in another embodiment the Processing functionality may reside within computing device 150.

Also connected to the network 190 may be a Web Server 147.

In the embodiment of FIG. 1, a computerized advanced processing rules data structure 160 is also coupled to the network 190. The computerized advanced processing rules data structure may exist in a number of forms, for example as a table, file, database, and/or other electronic data structure. The rules data structure 160 may include a listing of computerized advanced processing (CAP) that are available for use, for example by device 150. Particular CAP may be associated with various criteria, such as based on modality, description, patient information, clinical indication, medical facility, requesting doctor, image attributes, series type or description, and the like. For example, one or more CAP may be automatically selected for a particular image, series of images, and/or imaging exam (for example, which may include one or more image series) based on attributes of an image, series of images, and/or imaging exam, among other attributes. An image series may comprise one or more images. The rules data structure 160 may further include criteria for when certain CAP are automatically executed (for example, before the exam is sent to the radiologist for review) and/or whether confirmation is required before execution (for example, the radiologist may need to confirm that a particular CAP is performed). The rules data structure 160 may include rules for executing a particular CAP based on results of a first one or more CAP (that may have been automatically performed). Thus, in some embodiments multiple CAP may be selected and performed based on the various rules in the rules data structure 160. In some embodiments, the rules may include user, user group, site, and/or other preferences for selection and/or execution of CAP.

In the embodiment of FIG. 1, a computerized advanced processing (CAP) communication preferences data structure 160 is also coupled to the network 190. In various embodiments the CAP communications preferences data structure may be a file, table, database, and/or other electronic structure capable of holding communication preferences information. The CAP communications preferences data structure may contain information regarding how results of CAP are to be communicated. For example, some CAP results may be considered significant, as defined, for example, in CAP rules data structure 160. The CAP communications preferences may contain information regarding how significant results should be communicated (for example, differently than non-significant results). For example, a particular physician may indicate that certain types of significant results are to be communicated to him automatically via his smartphone, for example, using a push notification or text message. In another example, CAP communications preferences may specify that as soon as any CAP detects a significant result, that the results should be automatically communicated to the radiologist on call via his pager so he can immediately view the case, confirm the significance of the CAP result, and contact the appropriate physician caring for the patient.

In other embodiments, other computing devices that store, provide, acquire, and/or otherwise manipulate medical data may also be coupled to the network 190 and may be in communication with one or more of the devices illustrated in FIG. 1, such as with the computing device 150.

Depending on the embodiment, devices other than the computing device 150 that are illustrated in FIG. 1 may include some or all of the same components discussed above with reference to the computing device 150.

Figure 2:
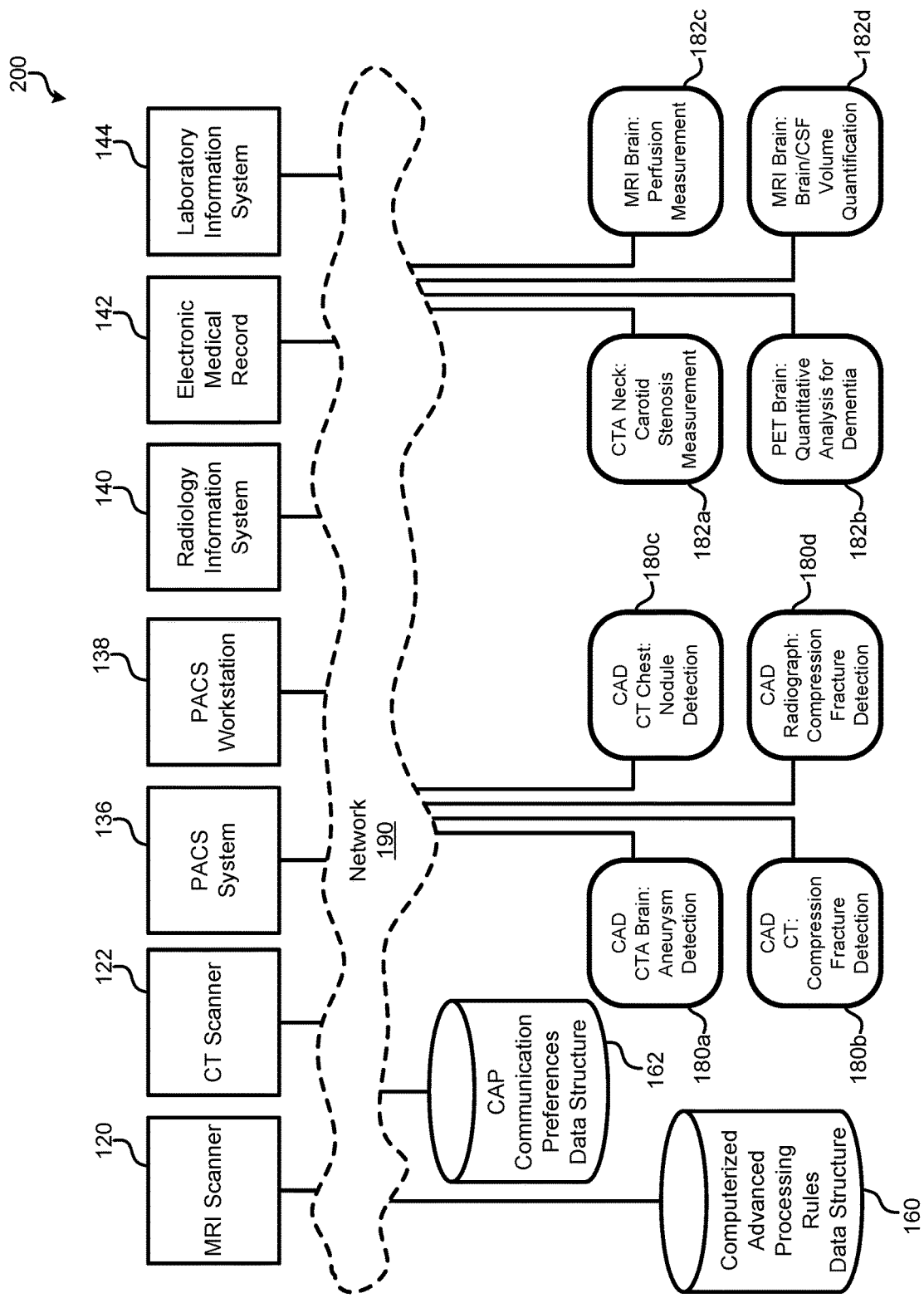

FIG. 2 is a system diagram which shows various components of a system 200, many of which are discussed above with reference to FIG. 1. In the example of FIG. 2, several specific CAP are illustrated, including various CAD processes (for example, CAD process 180a, 180b, 180c, and 180d), and other processing (for example, stenosis measurement 182a, dementia analysis 182b, perfusion measurement 182c, and volume quantification 182d). Each of these processes may be associated with a software module that is executable by various computing devices, such as the CAD systems 148, processing systems 149, the device 150, any other device(s) illustrated in FIGS. 1, 2, and/or 3, and/or any other suitable computing device. The CAP rules data structure 160 may include identification information for each of the processes 180 and 182, such as information on how each computerized advanced processing can be initiated, such as hardware addresses for devices that perform each process and/or identification information for the particular process (for example, that may be used to initiate a particular CAP, even if multiple CAP are performed by a single computing device). In other embodiments other types of CAP may be utilized. In one embodiment, an information display computing device, such as computing device 150 (FIG. 1) and/or computing device 250 (FIG. 3) may be in communication with any of the devices illustrated in FIG. 2 via the network 190.

Figure 3:
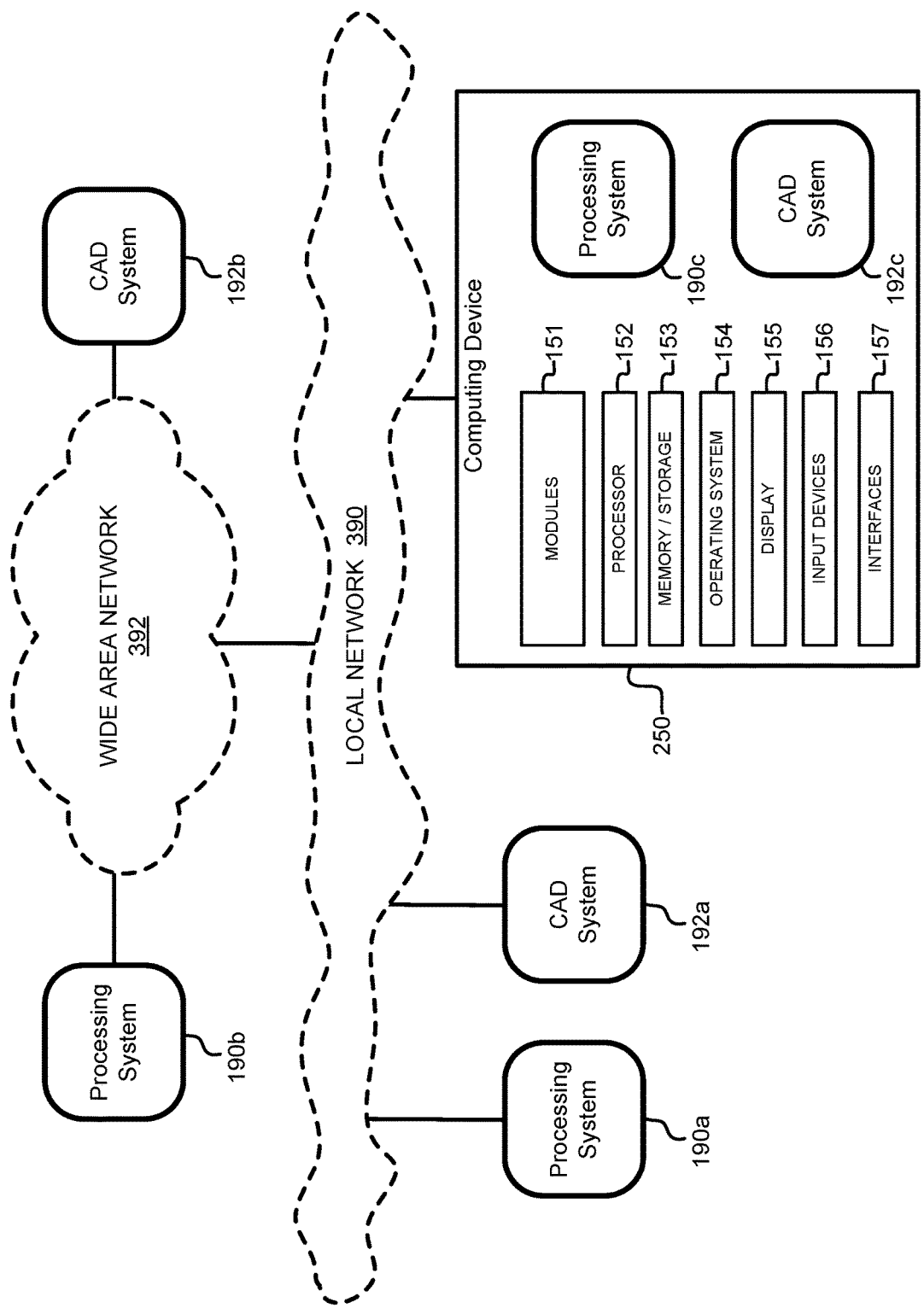

FIG. 3 is a block diagram of another network configuration of a computing device 250, which includes many of the same components discussed above with reference to computing device 150, and multiple CAD and processing systems. In this particular configuration, the CAD system 192a and/or Processing system 190a may be accessible to the computing device 250 via a local network 390, such as a secure local area network (for example, within a hospital or medical complex). The computing device may also access CAD system 192b and/or processing system 190b via a wide area network (WAN) 392, such as the Internet. Access to the WAN 392 may include communication through the local network 390 or may be directly between the computing device 250 and the WAN 392 in other embodiments. In the example of FIG. 3, the computing device may also include a CAD system 192c and processing system 190c, such as in the form of software modules that are stored on the computing device 250 and executable by the computing device. In other embodiments, a computing device, such as computing device 250 may access CAP systems/modules that are accessible in any one or more combinations of the above-noted manners, such as directly (for example, stored on the computing device), via a local network (for example, a local server executes the CAP module), and/or via a wide area network (for example, a remote server is contacted via the Internet and executes the CAP modules).

Example Rules for Selection of One or More Computerized Advanced Processing

FIG. 4A is a table illustrating an example of rules that may be stored in the CAP rules data structure 160 and/or otherwise accessed in order to automatically determine one or more CAP to perform on an image, image series, and/or imaging exam. In this example, the table (which may be any other data structure in other embodiments) indicates associations between particular modalities (column 402), exam types (column 404), and CAP (column 406) that may be valuable to examination of the exam images. The table further includes a rules column 408 that includes rules for execution of the CAP indicated in column 406. The rules may indicate that certain CAP are performed automatically (for example, without any input from the radiologist), automatically if certain conditions are met (for example, insurance covers, exam has certain characteristics, previous CAP has certain results, and the like), or after confirmation from a radiologist, for example. In the example rules 408, words in quotes indicate clinical indication or history, such as "trauma." The rules may further include other criteria for executing one or more CAP, for example based on one or more of:

Which CAP systems are available

Exam characteristics, for example, MRI of spine vs. CT of brain

Clinical information, for example, brain MRI where clinical question is dementia (one type of processing) vs. trauma (another type of processing)

User preference

Site preference

Insurance approval

Billable status

Referring does order

Presence of comparison exam

Whether or not a certain type of CAP was already performed on the exam and/or on a prior exam, for example:

If prior exam used CAD, automatically compare to result.

If prior exam used Quantitative Analysis, automatically compare to result.

Results of another CAP. For example, a rule may indicate that a particular CAP should be run if another specific CAP had a certain result (for example, another CAP had a result that was abnormal, normal, demonstrated a particular finding, demonstrated a measurement in a particular range, and/or the like).

Status of another CAP. For example, a rule may indicate that two CAP should be performed, but that a second CAP should not be performed until the first CAP is complete. By way of example, "Brain aneurysm detection CAD" may require that a "3D Vessel tracking" CAP be run first, as "Brain aneurysm detection CAD" may process the results of "3D Vessel tracking" CAP. The last example rule listed in the example CAP Rules table of FIG. 4B (described below) illustrates another example in which three CAP are automatically run in a particular sequence in the event that two conditions are met.

In some embodiments certain results of a CAP may automatically trigger the scheduling of another CAP (for example, based on the rules in column 408). For example, the modality and exam in rule 410 is associated with Brain MRI exams (as indicated in columns 402 and 404), and the indicated CAP of "MRI brain volumetric analysis" is associated with a rule (column 408) indicating that the CAP is automatically performed when the clinical indication is "dementia."

In some embodiments, scheduling of a particular CAP, either automatically or manually, may automatically cause one or more other CAP to be scheduled before or after that particular CAP. For example, exam rule 412 indicates that scheduling of "Brain aneurysm detected CAD" should result in the automatic scheduling of "3D Vessel tracking" CAP, and that "3D Vessel tracking" CAP should be run before "Brain aneurysm detected CAD", for example because "Brain aneurysm detected CAD" involves processing the results of "3D Vessel tracking" CAP.

In another example, the modality and exam in rule 411 is associated with Brain MRI exams (as indicated in columns 402 and 404), and the indicated CAP of "MRI brain CSF analysis" is associated with a rule (column 408) indicating that the CAP is automatically performed when the clinical indication is "hydrocephalus," "dementia," or there is an abnormal brain volumetric analysis from another CAP.

Thus, in an embodiment, the first CAP in rule 410 ("MRI Brain volumetric analysis") may first be automatically performed on a brain MRI, such as in response to an indication of "dementia" in the MRI order from the referring doctor. Once the MRI brain volumetric analysis has been performed, the rules of FIG. 4A may again be applied to determine if one or more additional CAP should be performed. In this example, if the result of the MRI brain volumetric analysis is "abnormal" (or equivalent nomenclature), another CAP listed in rule 411 (MRI brain CSF analysis) is triggered for automated execution. Thus, in various embodiments, the rules may be configured to initiate execution of multiple CAP in response to results of previously performed CAP.

In one embodiment, a rules data structure may be used to determine which CAP are compatible and/or available for a particular one or more image series, such as based on various characteristics associated with the one or more image series. For example, a rules data structure comprising modality, exam, and CAD/processing, such as columns 402, 404, and 406 in the example of FIG. 4A, may be used to determine which of the various CAD/processing are compatible with medical images in particular exam modalities and exams. In one embodiment, this information may be presented to users. In the example of rows 410 and 411, "MRI brain volume analysis" and "MRI brain CSF analysis" are listed as compatible and/or available for MRI exams of the brain.

In various embodiments, different rules may apply to different users and/or different user groups (for example, based on preferences of the users and/or user groups).

FIG. 4B is a table illustrating an example of rules that may be stored in the CAP rules data structure 160 and/or otherwise accessed in order to automatically determine one or more CAP to perform on an image or image series.

In various embodiments, rules related to CAP may be evaluated automatically, for example when:

An exam is completed on a scanner.

An exam is communicated, for example, from a scanner to a PACS System or from a PACS System to a PACS Workstation.

A CAP is performed, for example, such that the result of the CAP may automatically trigger performance of another CAP.

In various embodiments, evaluation of rules related to CAP may be performed on one or more computing devices, such as scanners, PACS Systems, PACS Workstations, and the like. Based on the evaluation of rules related to CAP, one or more CAP may be automatically executed.

Figure 4C:
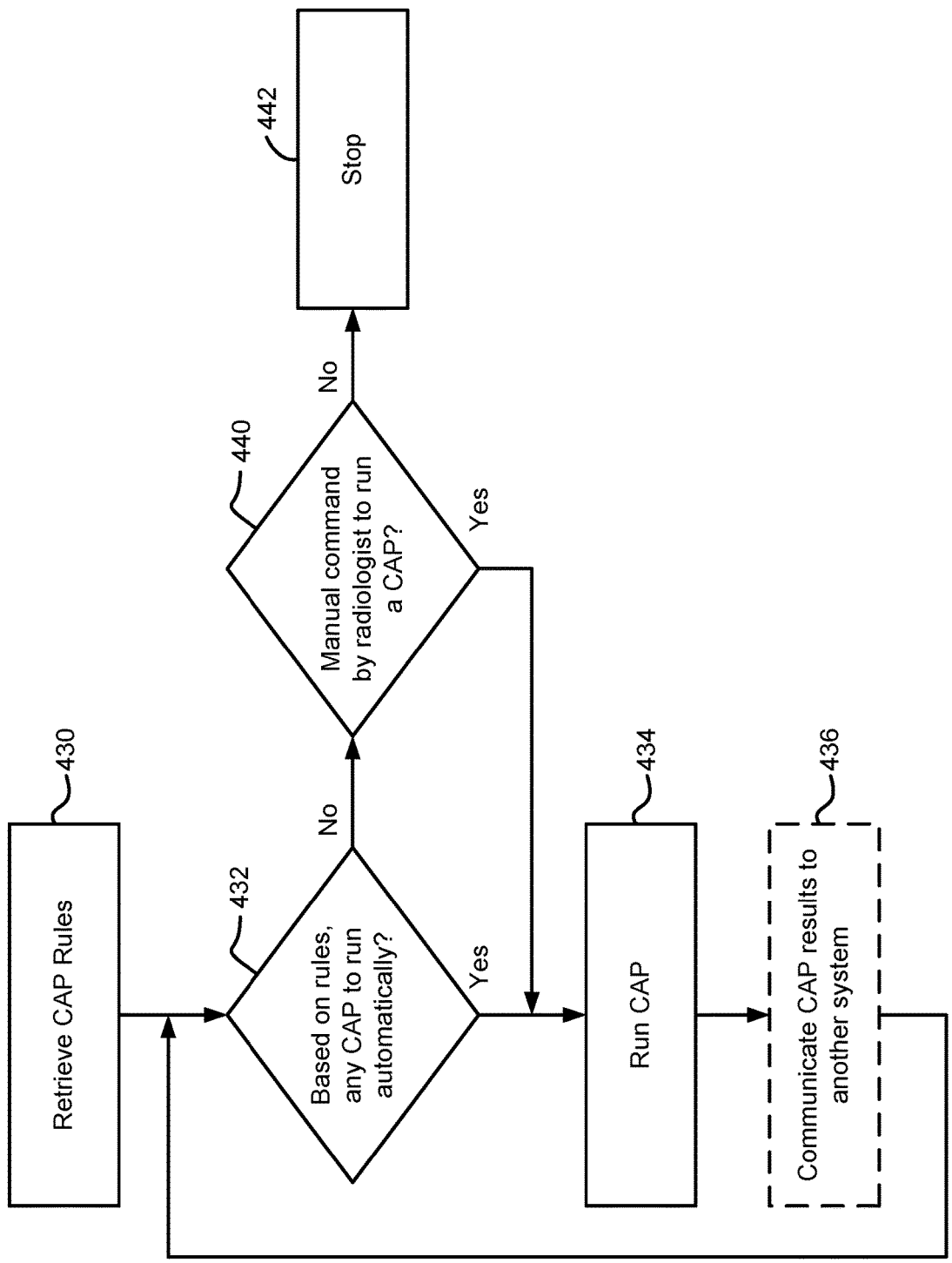
FIG. 4C is a flowchart illustrating an example process for running computerized advanced processing automatically or manually, according to an embodiment of the present disclosure.

FIG. 4C is a flowchart illustrating an embodiment in which CAP may be run automatically or manually. In various embodiments, the flowchart of FIG. 4C may include more or fewer blocks, and/or various blocks may be combined or divided into additional blocks. In various embodiments, the operations and/or processes shown in the flowchart of FIG. 4C and described below may be performed by, for example, CAD systems 148, processing systems 149, device 150, device 250, and/or any other device(s) illustrated in FIGS. 1, 2, and/or 3, and/or any other suitable computing device. For example, the operations and/or processes shown in the flowchart of FIG. 4C may be embodied in one or more software modules including computer executable instructions and executable by one or more hardware processors. For purposes of illustration, the blocks are discussed below as being performed by computing device 150.

At block 430, the computing device 150 accesses CAP rules that are usable to determine when CAP are run or retrieved, for example, rules 408 and/or the rules of FIG. 4B that are stored in one or more rules data structures, such as CAP Rules Data Structure 160.

At block 432, the computing device 150 evaluates the CAP rules in order to determine if one or more CAP should be executed, for example, based on modality, exam type, clinical indication, ordering physician preference, reading radiologist preference, insurance approval, results of other CAP, and the like.

If the computing device determines, at block 432, that there is no CAP to run automatically, the computing device 150 optionally accepts input from a radiologist, or other user indicating a CAP to be manually run. Such input from the radiologist may be received by the radiologist providing, for example, an input to the device 150 (and/or any other suitable computing device). If the input indicates that no CAP should be run, then no more action occurs within this logic, as indicated by block 442.

At block 434, a CAP is run, either because one was automatically selected at block 432, or because a manual command was received at block 440. In optional block 436, results of the CAP performed may be communicated to other processes. In one embodiment, the CAP results may be automatically communicated to various users. In one embodiment, CAP results may be communicated to a system used to create reports, such as Radiology Information System 140. Example embodiments are discussed herein with reference FIGS. 7A, 7B, and 8.

At block 436 (or block 434 if block 436 is not included), the logic loops back to block 432 to determine whether additional CAP should be run. As discussed above, CAP rules may cause CAP to run based on the result of one or more other CAP. For example, a rule for executing a particular CAP may not have been met in a first run of blocks 432 and 434, but the rule may be met in a subsequent run of block 432 based on results of a CAP that was performed at block 434 of the first run.

Example User Interfaces

FIG. 5 illustrates a sample display device (for example, a portion of one of the computing devices 150 or 250) with status information regarding CAP that are scheduled, in progress, and/or completed (and/or other statuses). In some embodiments, CAP may require relatively long periods of time to process. For example, certain CAP use complex computer algorithms that require relatively long periods of time to execute. Additionally, in cases where CAP occurs remotely (for example, by a CAP server in communication via the Internet), communication time (for example, transfer of exam images and/or results) may be increased.

In some instances, users (for example, radiologists) may desire that all applicable CAP are complete before they view an exam. Thus, in some embodiments the modules 151 are configured to generate one or more user interfaces (UIs) that indicate status of various CAP. In the example of FIG. 5, a UI is shown that includes a patient list and status indications for each CAP associated with a particular exam of the patient. Thus, in various embodiments, a user may elect to choose exams to read that have completed CAP and/or delay choosing exams where processing is incomplete.

In systems wherein exams are automatically chosen for reading (for example, downloaded to a particular workstation automatically and/or automatically prioritized), either on-the-fly or via building work lists, CAP statuses may be utilized. For example, a PACS workstation or other computing device (for example, computing device 150 or 250) may automatically retrieve exams for the user to read based on a number of factors, such as CAP completion status, exam status (Stat, routine, and the like), exam description, exam date, user's specialty, user preference, and/or any other related criteria. Thus, in some embodiments, the user may have a preference not to have exams still undergoing CAP (for example, status is not complete) included on a worklist for the user. In another embodiment, the completion status of CAP may be ignored for exams that have certain characteristics, such as those marked as STAT, otherwise emergent, and/or have some other characteristic. In another embodiment, a result of CAP, such as a result designated as a critical result, may cause a user to be automatically notified of the result and/or the exam to be prioritized in the reading queue.

Figure 6:
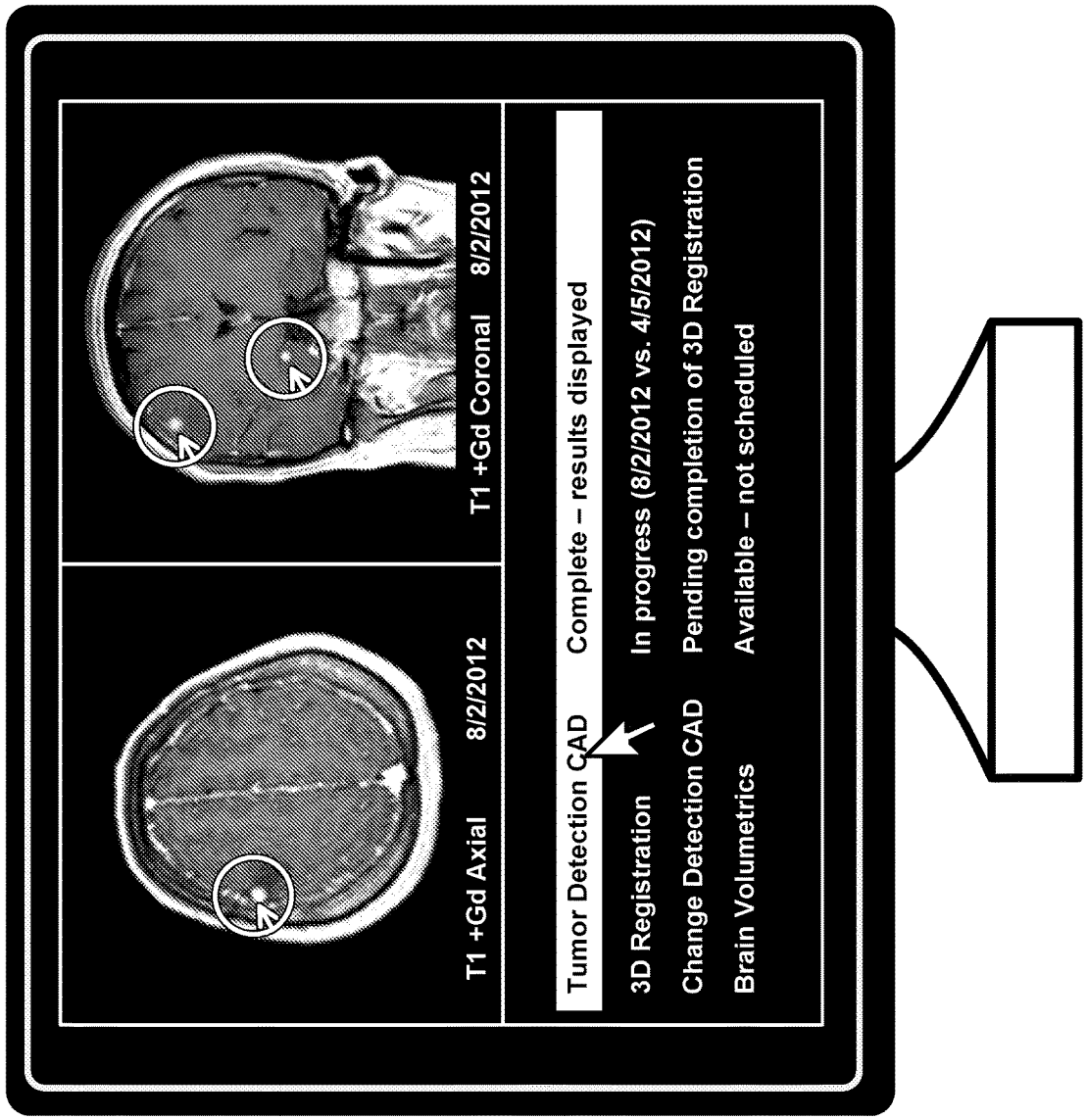
FIG. 6 illustrates an example user interface in which status information and medical images with notations are displayed, according to an embodiment of the present disclosure.

FIG. 6 illustrates a sample display device (for example, a portion of one of the computing devices 150 or 250) depicting CAP status information, as well as medical images including notations from one or more CAP. In various embodiments, the sample UI of FIG. 6 allows users, such as radiologists, viewing exams on a computing device to be aware of various aspects of CAP operations. In one embodiment, available types of CAP applicable to the exam type are listed with status. In this embodiment, a user (for example, a doctor) may indicate CAP to be performed and control which CAP indicators are displayed.

In various embodiments, a user interface such as the UI of FIG. 6 may display one or more of:

The various CAP available and relevant to the exam being viewed.

Which CAP systems have been selected to process the exam, either because they were automatically or manually chosen.

The status of CAP, for example, pending, in progress, complete, and the like.

Which CAP have been run.

Which CAP doctors have viewed and/or acknowledged.

Which CAP results are/are not in the report.

Which CAP have detected an important or critical result.

Whether the appropriate manual and/or automatic actions have been performed for communication of detected important/critical results.

Results of one or more CAP may include information that may be important for one or more users (for example, radiologist, referring doctor, and the like) to view. For example, in the case of CAD systems, in various embodiments the results may be one or more indicators that are superimposed on images to indicate to the user one or more of:

The location of a detected abnormality.

The "type" of a detected abnormality, for example, aneurysm vs. stenosis in a vascular analysis CAD system.

For each detected abnormality, a level of confidence that the abnormality is present.

In various embodiments, certain CAP may determine one or more sets of indicators that may be superimposed on the images. In the embodiment of FIG. 6, the user has the ability to select indicators for display from any of one or more CAP that were performed on the displayed image, series, or exam. In the example of FIG. 6, the user has chosen to display indicators that show where a Tumor Detection CAD system has identified lesions. In the example shown, the indicators comprise a circle and internal arrow centered on the location of a detected lesion. In one embodiment, when the user selects another completed CAP (or at least partially completed CAP) listed in the GUI, the information related to the selected CAP is displayed, such as indicators superimposed on the images. In one embodiment, the user can include indicators from multiple CAP concurrently on displayed images. In one embodiment, the user may click or otherwise select a CAP to cause the results of the CAP to be displayed.

In the example of FIG. 6, the UI indicates that "Tumor Detection CAD" is both complete and the results are currently being displayed (black text on a white background vs. the other lines which show white text on a black background).

The UI further indicates that "3D Registration" is in progress and that the exams being registered are the exams dated Aug. 2, 2012, the current exam being viewed, and the exam of Apr. 5, 2012. In another embodiment, in addition to the dates of the exams being registered, other information about the exams may be displayed, for example, a modality, an exam type, an exam time, and the like. In one embodiment, the user may hover over or click on an item in the status list in order to view other information, for example, exam type, modality, exam type, and/or estimated time for completion of the CAP in progress, among other information. The other information may be displayed, for example, in a popup frame or under the status line.

The UI further indicates that the "Change Detection CAD" has been scheduled, and will be run after another CAP is complete, "3D Registration" in this example. The example UI of FIG. 6 further indicates that the "Brain Volumetrics" CAP is available, but not scheduled.

In one embodiment, the user may click or otherwise select a CAP that has not been scheduled to cause it to be scheduled and/or change its priority with reference to other CAP. In one embodiment, additional information may be displayed, e.g., the estimated time for completion of the listed CAP or in indictor showing its completion status, e.g., a bar demonstrating that a cap is 60% completed.

Reporting CAP Results

There is a need to manage how the results of CAP are communicated, for example via reports of exams and/or other means (for example, automatic communication to a doctor interpreting the exam, a doctor who ordered the exam, a doctor providing care for the patient, an electronic medical record, or a database). In one embodiment, the modules 151 (and/or other systems that coordinate selection and initiation of various CAP as discussed above) are configured to automatically put CAP results in a report associated with an exam. The modules 151 may automatically alert a user (for example, a doctor) if a CAP detects a significant abnormality in an exam that has not yet been viewed. In another embodiment, when a CAP detects a result that is designated as significant or emergent (for example, based on rules stored in Computerized Advanced Processing Rules Data Structure 160) the result may be automatically communicated, for example, to one or more of a doctor who ordered the exam, a doctor providing care for the patient, an electronic medical record, a database, and/or the like. In one embodiment, automatic communication of a significant or emergent result detected by a CAP may occur before the exam has been viewed by a user. In one embodiment, automatic communication of a significant or emergent result detected by a CAP may occur after the exam has been viewed by a user.

In one embodiment, alerts and/or other actions to be taken based on results of one or more CAP may be stored in an alert data structure that contains rules for providing alerts and/or taking other actions. For example, rules may indicate that important or other types of results generated by CAP result in automatic action, for example automatic alerting of a user or other communication of results. The alert data structure may include multiple delivery options, such as delivery mediums (for example, email, SMS, phone, etc.), delivery schedules (for example, only certain alerts may be delivered outside of pre-set work hours), destinations (for example, certain alerts may go to an entire medical group, while others only go to a referring physician), and/or other similar alert parameters. In one embodiment, the alert data structure stores results of performed CAP(s) that may be included in alerts, either before or after a report is generated and/or marked as read.

Figure 7B:
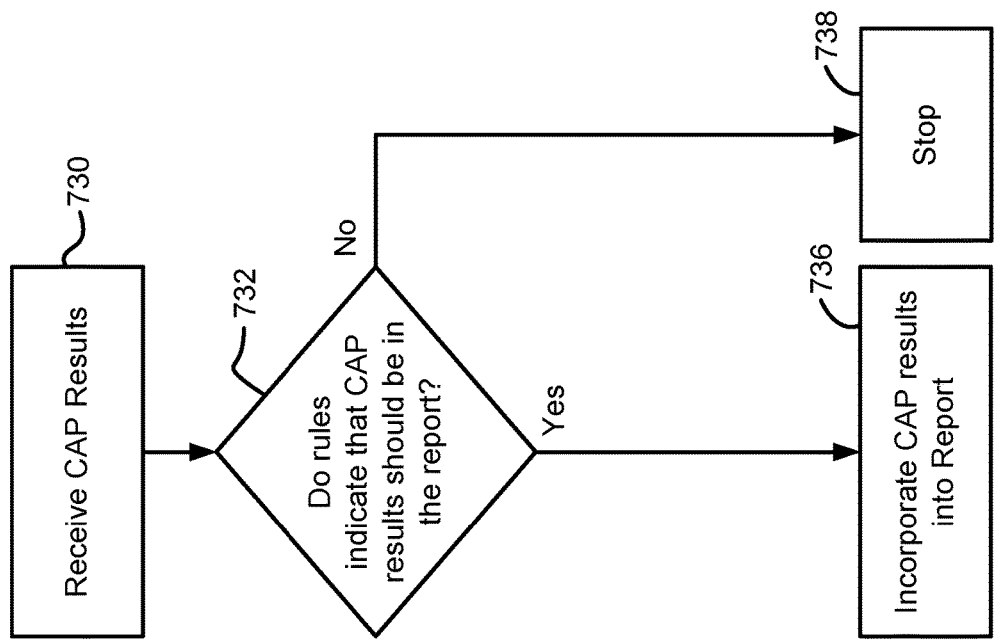
FIGS. 7A-7B are flowcharts illustrating example processes of computerized advanced processing, according to various embodiments of the present disclosure.
Figure 7A:
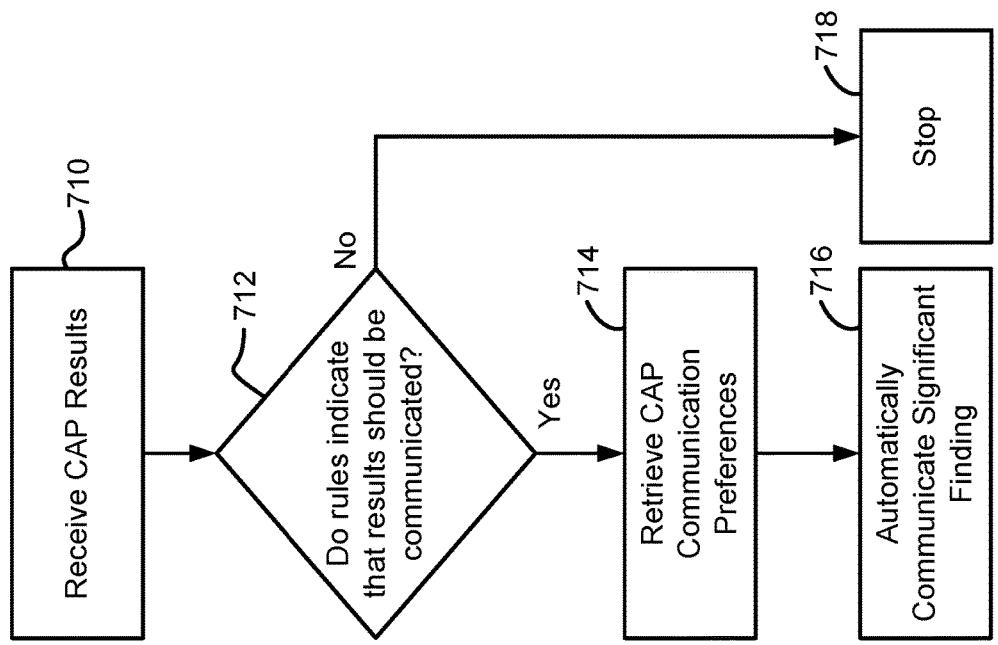

FIG. 7A is a flowchart illustrating an embodiment in which certain results of CAP are automatically communicated. In various embodiments, the flowchart of FIG. 7A may include more or fewer blocks, and/or various blocks may be combined or divided into additional blocks. In various embodiments, the operations and/or processes shown in the flowchart of FIG. 7A and described below may be performed by, for example, CAD systems 148, processing systems 149, device 150, device 250, any other device(s) illustrated in FIGS. 1, 2, and/or 3, and/or any other suitable computing device. For example, the operations and/or processes shown in the flowchart of FIG. 7A may be embodied in one or more software modules including computer executable instructions and executable by one or more hardware processors. For purposes of illustration, the method of FIG. 7A will be described below as performed by the computing device 150.

At block 710, results of a CAP and/or an indication that results of the CAP are available are received by the computing device 150.

Next, at block 712 the received CAP results are evaluated in light of CAP processing rules to determine if the CAP results are to be automatically communicated to one or more users, devices, systems, etc. In one example, the CAP processing rules may indicate that only significant results may be communicated automatically (and may include criteria for what qualifies as a significant result), whereas in another example all results may be automatically communicated, depending on rules configured for individuals, groups, and/or sites.

If the computing device 150 determines, at block 712, that the CAP results are to be automatically communicated, the method continues to block 714 wherein CAP communication preferences are retrieved, for example, from CAP Communication Preferences Data Structure 162. For example, CAP communication preferences may indicate that a significant finding detected by CAP, such as detection of a pneumothorax on a chest x-ray or chest CT scan, is to be treated as a significant finding requiring immediate communication. Information in the CAP Communications Preferences Data Structure may indicate that significant findings be communicated automatically to the ordering physician, the hospitalist currently caring for the patient, and/or the radiologist current reading cases or on call. Information in the CAP Communications Preferences Data Structure might also include the preferred method of communication set by each user, for example, text, email, phone call, and/or the like.

Moving to block 716, the CAP results are automatically communicated based on the preceding determinations, such as to one or more users, devices, systems, etc., via one or more communication mediums, and including certain portions of the CAP results possible in custom formats. Thus, CAP results may be sent to two different users via different communication mediums (e.g., one via email and another via text message) including different portions of the CAP results (e.g., all of the report in an email vs. only a summary of the report in a text message). In one embodiment, automated communications are automatically logged. When it is determined that no results to be automatically communicated, the process stops at block 718.

In various embodiments, the modules 151 may further be configured to provide one or more of various alerts as an exam is being viewed. For example, the modules 151 may be configured to initiate alerts to the user in response to one or more of:

User closes an exam or attempts to mark exam as read before all scheduled CAP is complete.

User closes an exam or attempts to mark exam as read without viewing all CAP results (or CAP results with at least a threshold importance).

User closes an exam or attempts to mark a case as read without acknowledging CAP results.

User attempts to mark report as complete and CAP results are not included in a report.

User attempts to mark report as complete and important or critical CAP results are not included in a report.

User attempts to mark report as complete while critical or other types of results have not been communicated, for example, to the ordering physician, or processed for communication has not been initiated.

FIG. 7B is a flowchart illustrating an embodiment in which results of CAP are automatically incorporated into reports, such as radiology reports created by radiologists related to medical imaging exams, utilizing, for example. Radiology Information System 140. In various embodiments, the flowchart of FIG. 7B may include more or fewer blocks, and/or various blocks may be combined or divided into additional blocks. In various embodiments, the operations and/or processes shown in the flowchart of FIG. 7B and described below may be performed by, for example, CAD systems 148, processing systems 149, device 150, device 250, any other device(s) illustrated in FIGS. 1, 2, and/or 3, and/or any other suitable computing device. For example, the operations and/or processes shown in the flowchart of FIG. 7B may be embodied in one or more software modules including computer executable instructions and executable by one or more hardware processors. For purposes of illustration, the method of FIG. 7B will be described below as performed by the computing device 150.

Beginning at block 730, results of a CAP and/or an indication that results of the CAP are available are received by the computing device 150.

At block 732, rules are evaluated to determine whether the CAP results should be incorporated into a medical report and/or other document or file. These rules may be stored in CAP Rules Data Structure 160. By way of example, a rule may indicate that only positive CAP results be included in the reports. For example, if significant midline shift is detected by a computer aided diagnosis system, a form of CAP that may be used to evaluate a brain CT, the significant result may be automatically included in the report. In another example, another rule may indicate that all CAP results, or some other subset of results that are selected based on rule criteria, are automatically incorporated into the report, regardless of the result, such as a CSF volumetric assessment of a brain MRI. Rules may incorporate preferences of individual users, groups, and/or sites. For example, one radiologist may configure the system so that the results of a particular CAP are automatically incorporated into his reports, while another might indicate that the CAP results should not be automatically incorporated.

At block 736, the CAP results are incorporated into the report. Alternatively, when it is determined that no CAP results are to be included in the report, the process stops at block 738.

Figure 8:
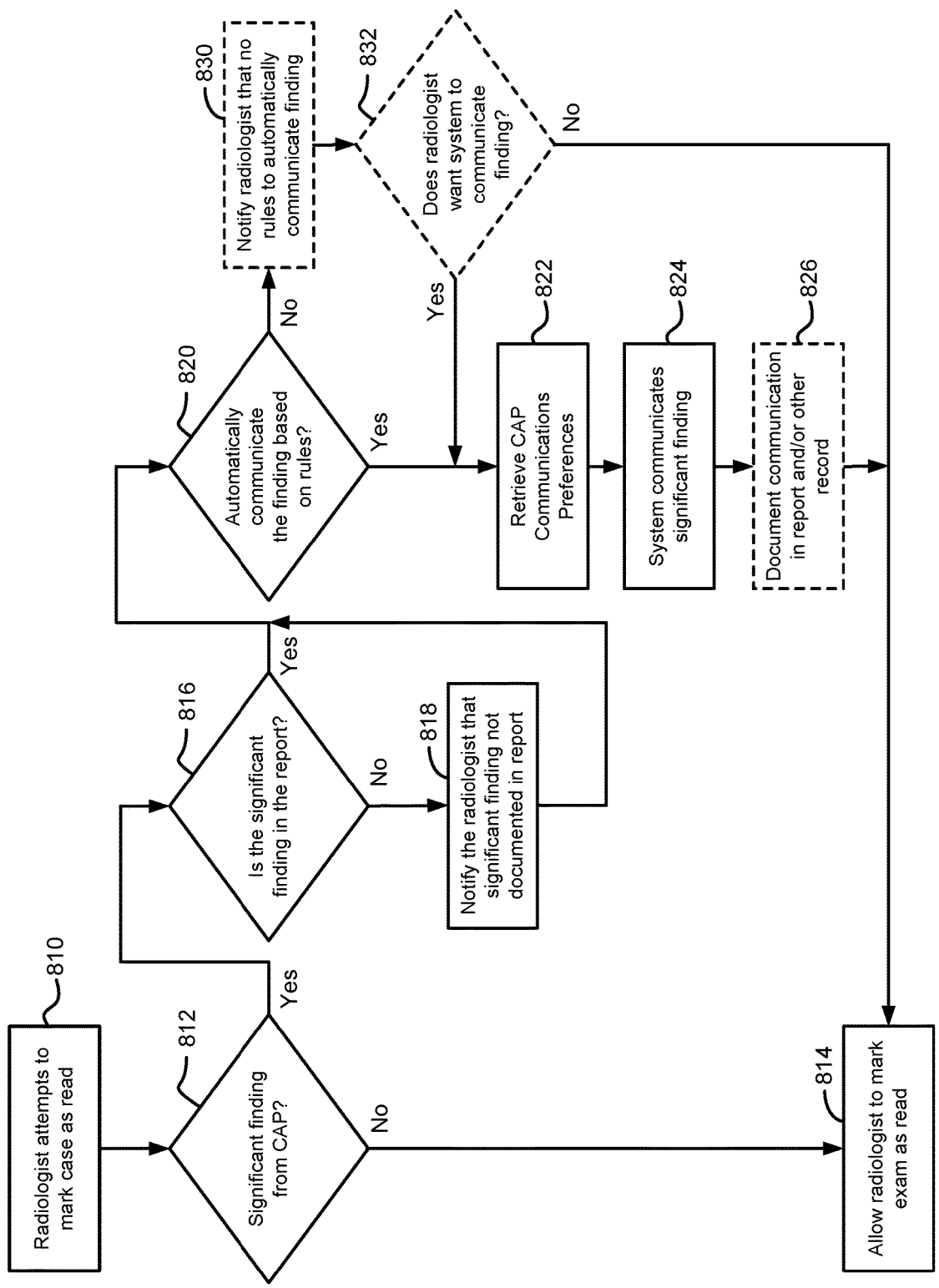
FIG. 8 is a flowchart illustrating another example process of computerized advanced processing, according to an embodiment of the present disclosure.

FIG. 8 is a flow chart that illustrates an embodiment that operates in relation to a radiologist creating a report on a medical exam where there are related CAP results. In various embodiments, the flowchart of FIG. 8 may include more or fewer blocks, and/or various blocks may be combined or divided into additional blocks. In various embodiments, the operations and/or processes shown in the flowchart of FIG. 8 and described below may be performed by, for example, CAD systems 148, processing systems 149, device 150, device 250, any other device(s) illustrated in FIGS. 1, 2, and/or 3, and/or any other suitable computing device. For example, the operations and/or processes shown in the flowchart of FIG. 8 may be embodied in one or more software modules including computer executable instructions and executable by one or more hardware processors. For purposes of illustration, the method of FIG. 8 will be described below as performed by the computing device 150.

Beginning at block 810, a radiologist or other reader attempts to mark the exam he is reading as "read," indicating that he has completed his evaluation of the exam and desires to finalize the report on the exam.

At block 812, the system determines whether or not a significant finding was detected by a CAP run on the exam. Rules determining which results are "significant" may be stored in a data structure, such as CAP Rules Data Structure 160. Rules may be set by various users, such as individual radiologists and/or ordering physicians, and/or by groups of users. For example, detection of a subdural hematoma by a CAD processing of a brain CT may be an example of a significant finding.

At block 812, if it is determined that no significant finding was detected by CAP associated with the exam, then the radiologist may mark the exam as read at block 814.

Alternatively, at block 812, if it is determined that a significant finding was detected, then at block 816, the system may determine whether or not the significant finding is documented in the report, for example, because it was automatically added by the system or manually added by the radiologist.

If the significant finding is not in the report, then at block 818 the radiologist is notified that the significant finding is not documented in the report so that he has the opportunity to add the finding to the report. In various embodiments, the radiologist may be notified by, for example, a visual, audible, and/or tactile indicator. For example, the radiologist may be prompted by a message or flashing indicator on the display, or an audible alarm. If, at block 816, it is determined that the significant finding is in the report, the system proceeds to block 820.

At block 820, CAP processing rules are used to determine whether or not the significant finding should be automatically communicated, for example, to the physician caring for the patient and/or the physician who ordered the imaging exam. If it is determined that there are no rules that indicate that the significant finding should be automatically communicated, then at optional block 830 the radiologist is notified that the system is not going to automatically communicate the significant finding. At optional block 832, the radiologist may indicate that he would like the system to communicate the findings, for example, to the physician caring for the patient.

At block 822, performed in preparation for communicating the finding, CAP communications preferences are retrieved, for example, from CAP Communication Preferences Data Structure 162, to determine the mode of automated communication, for example, text, pager, email, phone call, and/or the like.

At block 824, the significant finding is communicated to the designated and/or indicated user. At optional block 826, the results of the automated communication may be automatically documented, for example, in the report and/or another record.

Other Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an information display computing device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

What is claimed is:

1. A computing system comprising:
one or more hardware computer processors configured to execute software instructions; and
one or more electronic storage devices in communication with the one or more hardware computer processors and storing software modules, the software modules comprising software instructions configured for execution by the one or more hardware computer processors in order to cause the computing system to:
access, from one or more image storage devices; an image series comprising one or more medical images;
determine an exam characteristic associated with the image series, the exam characteristic including a result of a previously run computerized advanced processing technique, the processing run computerized advanced processing technique including one selected from a group consisting of volumetric rendering, multiplanar reconstruction, maximum intensity projection, quantitative analysis, and computer-aided diagnosis;
access, from a computerized advanced processing data structure, rules for execution of respective computerized advanced processing techniques, the rules indicating:
one or more associations between exam characteristics and corresponding computerized advanced processing techniques, the exam characteristics including at least a modality and exam type; and
one or more criteria associated with respective computerized advanced processing techniques for automatically initiating execution of corresponding computerized advanced processing techniques;
determine, based on the rules, one or more computerized advanced processing techniques associated with the determined exam characteristic of the image series; and
for each of the determined computerized advanced processing techniques:
in response to determining that criteria associated with the computerized advanced processing technique are satisfied, automatically initiate execution of the computerized advanced processing technique on the image series.

2. The computing system of claim 1, wherein the software modules are further configured for execution by the one or more hardware computer processors in order to cause the computing system to:
determine an additional computerized advanced processing technique associated with the determined exam characteristic of the image series, the determined exam characteristic including criteria indicating the result of the another computerized advanced processing; and
in response to determining that criteria associated with the additional computerized advanced processing technique are satisfied, automatically initiate execution of the additional computerized advanced processing technique on the image series.

3. The computing system of claim 1, wherein the software modules are further configured for execution by the one or more hardware computer processors in order to cause the computing system to:
compare results of the executed computerized advanced processing techniques to one or more results indicated in an alert data structure; and in response to identifying a particular result of the executed computerized advanced processing techniques in the alert data structure, initiate transmission of an alert to one or more users and/or computing systems.

\* \* \* \* \*